(12) United States Patent
Lutsen et al.

(10) Patent No.: US 8,765,882 B2
(45) Date of Patent: Jul. 1, 2014

(54) POLYTHIOPHENE BASED ACTIVE LAYER FOR SOLAR CELLS

(75) Inventors: Laurence Lutsen, Coudekerque-Branche (FR); Dirk Vanderzande, Hasselt (BE); Bert Campo, Bouwel (BE)

(73) Assignees: IMEC, Leuven (BE); Universiteit Hasselt, Diepenbeek (BE)

( * ) Notice: Subject to any disclaimer, the term of this patent is extended or adjusted under 35 U.S.C. 154(b) by 18 days.

(21) Appl. No.: 13/491,934

(22) Filed: Jun. 8, 2012

(65) Prior Publication Data

US 2012/0279569 A1 Nov. 8, 2012

Related U.S. Application Data

(63) Continuation of application No. PCT/EP2009/066896, filed on Dec. 11, 2009.

(51) Int. Cl.
  *H01L 51/46* (2006.01)
  *C08L 81/00* (2006.01)

(52) U.S. Cl.
  USPC .................................................. 525/535

(58) Field of Classification Search
  USPC .................................................. 525/535
  See application file for complete search history.

(56) References Cited

U.S. PATENT DOCUMENTS

| | | | |
|---|---|---|---|
| 5,569,708 A * | 10/1996 | Wudl et al. | 524/607 |
| 6,166,172 A | 12/2000 | McCullough et al. | |
| 7,452,958 B2 * | 11/2008 | McCullough et al. | 528/73 |
| 2009/0211632 A1 * | 8/2009 | Brett et al. | 136/256 |

FOREIGN PATENT DOCUMENTS

| | | |
|---|---|---|
| WO | WO 87/05914 A1 | 10/1987 |
| WO | WO 2009/056496 A1 | 5/2009 |
| WO | WO 2009/100519 A1 | 8/2009 |

OTHER PUBLICATIONS

Chen et al., J. Am. Chem. Soc. (1992) 114, 10087).
Ego et al., Adv. Mater. 14 (2002) 809-811.
Milstein et al., J. Am. Chem. Soc. 1978, 100, 3636.
Milstein et al., J. Am. Chem. Soc., 1979, 101, 4992.

(Continued)

*Primary Examiner* — Mike M Dollinger
(74) *Attorney, Agent, or Firm* — Knobbe, Martens, Olson & Bear, LLP.

(57) ABSTRACT

New monomers, polymers, and blends of polymers with an electron acceptor are provided, e.g., for use in a photovoltaic device. The electron acceptor can be a fullerene derivative and the polymer can comprise monomer units according to the formula:

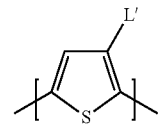

wherein L' is L-C(O)O-J, L-C(O)NR'-J, L-OCO-J', L-NR'CO-J', L-SCO-J', L-O-J, L-S-J, L-Se-J, L-NR'-J or L-CN; L is a linear or branched alkylene group having from 1 to 10 carbon atoms; J is a hydrogen atom or a linear or branched alkyl group having from 1 to 4 carbon atoms; J' is a group having from 1 to 10 carbon atoms, being saturated or unsaturated, linear or branched, optionally comprising a phenyl unit; and R' is a hydrogen atom or a linear or branched alkyl group having from 1 to 4 carbon atoms.

15 Claims, 18 Drawing Sheets

(56) References Cited

OTHER PUBLICATIONS

Yamamoto et al., Macromolecules, 1992, 25, 1214.
Campaigne et al., J. Am. Chem. Soc., vol. 77, 1955, 5425-5427.
Fabrichnyi et al., Chemistry of Heterocyclic Compounds, vol. 10, 1971, 1358-1360.
Gurovets et al., Chemistry of Heterocyclic Compounds, vol. 20, No. 12, 1984, 1331-1336.
Hoppe et al., J. Mater. Chem., vol. 16, 2005, 45-61.
Janssen et al., J. Chem. Phys. 103 (20) 1995, 8840-8845.
Janssen et al., Synthetic Metals 70, 1995, 1343-1344.
Kantam et al., Helvetica Chimica Acta, vol. 91 (2008), 1947-1953.
Mihailovic et al., J. Org. Chem., vol. 22, 1957, 652-654.
Muraro et al., Bulletin de La Societe Chimique de France, Jan. 1, 1973, 310-317.
Ego et al., J. Am. Chem. Soc. 125(2) (2003) 437-443.
Grimme et al., Adv. Mat. (1995) 7, 292.
McCullough et al., J. Chem. Soc., Chem. Commun., 1992. 70.
Miyaura et al., Suzuki. Synth. Commun., 1981, 11, 513.
Setayesh, S., Macromolecules (2000)33:2016.
Zhu et al., Journal of macromolecular science, part A, pure and applied chemistry, vol. 41, N° 12, pp. 1467-1487, 2004.

* cited by examiner

POLYTHIOPHENE BASED ACTIVE LAYER FOR SOLAR CELLS

CROSS-REFERENCE TO RELATED APPLICATIONS

This application is a continuation, under 35 U.S.C. §120, of International Patent Application No. PCT/EP2009/066896, filed on Dec. 11, 2009 under the Patent Cooperation Treaty (PCT), which was published by the International Bureau in English on Jun. 16, 2011, which designates the United States, the disclosure of which is hereby expressly incorporated by reference in its entirety and is hereby expressly made a portion of this application.

FIELD OF THE INVENTION

The present invention relates to new thiophene monomers, as well as conjugated polymers comprising the same. The present invention also relates to blends of conjugated polymers comprising new thiophene units with electro-accepting compounds, and opto-electronic devices, such as photovoltaic cells, made with such blends. The present invention also relates to methods for producing and polymerizing such new thiophene monomers.

DESCRIPTION OF THE RELATED ART

Conjugated polymers and in particular polythiophene polymers have been widely used in opto-electronic devices such as field-effect transistors and photovoltaic cells. For photovoltaic cells, polythiophene polymers are usually used as the electron donor and an electron acceptor is brought in contact with it in the device. Electron acceptors that have been used for this purpose are either other conjugated polymers bearing electron accepting groups or non-polymeric molecules such as fullerene or perylene imide derivatives. A promising photovoltaic structure comprises a bulk-heterojunction (BHJ) of an electron donor and an electron acceptor. In a bulk-heterojunction, the donor-acceptor interface is highly folded such that photogenerated excitons have a high probability of finding a donor-acceptor interface within a distance $L_D$ of their generation site. Bulk-heterojunctions are typically fabricated by spin-coating a mixture of soluble versions of the electron donor and electron acceptor materials. During spin coating and solvent evaporation, the donor and acceptor materials phase separate, creating an intricate interpenetrating network.

However, this network lacks stability and tends to demixing resulting in increased phase separation over time, thereby causing instability and continuous decrease in device performance characteristics. For instance, phase separation leads to a decrease in the surface of the donor/acceptor interface, to a decrease in exciton dissociation, to a decrease in the number of charges collected at the electrodes, to a decrease in short circuit current density ($J_{sc}$) and in power conversion efficiency.

One method of enhancing bulk heterojunction stability is to cross-link the network.

In the field of organic semi-conducting materials, the interest in crosslinkable materials is increasing, notably for electroluminescent devices and the application of the active layer in a direct structured manner, thereby avoiding the use of shadow masks.

Zhu et al (Journal of macromolecular science, part A, pure and applied chemistry, vol. 41, No 12, pp. 1467-1487, 2004) discloses an epoxy-functionalized fullerene $C_{60}$ derivative as well as cross-linkable polythiophene derivatives for the purpose of stabilizing film morphology in a bulk-heterojunction involving a mixture polythiophene—fullerene. The stabilizing effect was sought via the polymerization or cross-linking of these entities once the bulk-heterojunction is formed. The epoxy-functionalized fullerene $C_{60}$ derivative, once polymerized, was found to stabilize the phase-separated morphology. Cross-linkable polythiophene derivatives were also prepared but were much less effective in stabilizing film morphology. These techniques make use of photoinitiators and require UV light for the polymerization/cross-linking process. Such UV induced reactions involve the formation of radicals that are detrimental to the polymer structure.

The disadvantage of an admixed electronically active compound such as a photoinitiator is that its inclusion introduces a reactive impurity, which can adversely affect the film composition, the film morphology and then affecting the functioning of the organic device. This is even truer for organic devices such as organic bulk hetero junction solar cells in which the nano-morphology of the active layer is very sensitive to any parameter change (during the fabrication process but also over time after fabrication). Moreover, a cross-linking step was up to now believed to be required for stabilizing bulk heterojunction.

SUMMARY OF THE INVENTION

It is an object of the present invention to provide new thiophene-based polymers for enabling the manufacture of morphologically stable bulk-heterojunction photovoltaic cells without making use of a crosslinking step and without making use of photo-initiators to realize such a crosslinking step It has been surprisingly observed that a class of thiophene containing polymers has the unexpected ability to form stable bulk-heterojunction when blended with electron acceptors such as fullerene derivatives.

It is an advantage of some embodiments of the present invention that thiophene-based polymers can be produced that permit the stabilization in time of the nano-morphology of an active layer comprising said thiophene-based polymer. For instance, an active layer in organic bulk heterojunction solar cells comprising a thiophene-based polymer according to an embodiment of the present invention can have a stable nano-morphology without cross-linking of said material.

It is another advantage of some embodiments of the present invention that the physical stabilization of the morphology is accompanied by a stabilization of the performance characteristics of the device, such as for instance the power efficiency and/or the short circuit current of a bulk heterojunction solar cell.

It is another advantage of some embodiments of the present invention that the stabilization of the morphology is accompanied by an increase in the lifetime to predetermined performance levels of the devices, in particular solar cells.

It is another advantage of some embodiments of the present invention that the stability in time of the power efficiency of the solar cells may be linked to the stability in time of the active layer. This active layer may be processed as a thin film from an organic solvent in which both a polymer according to embodiments of the present invention (p-type, electron donor) and an n-type (electron acceptor) components are soluble, and may be made from a blend of a p-type polymer according to embodiments of the present invention and a n-type material (for example a $C_{60}$ fullerene derivative or a n-type semi-conducting polymer) which would tend to demix with time if the p-type material was not a polymer according to an embodiment of the present invention.

It is an object of the present invention to provide a stable active layer based on a blend of p-type and n-type materials for bulk heterojunction solar cell applications. This blend may be made of a p-type polymer comprising thiophene units having specific side chains and a n-type material mixed together in various ratios and processed e.g. as a thin film from solution. The n-type material included in such blends can be any molecule, oligomer or polymer able to accept an electron from the polymer according to an embodiment of the present invention. As a guideline, n-type materials known to operate an electron transfer when brought into contact with poly(3-hexyl-thiophene) (P3HT) can usually be used. This is true because the polymers according to embodiments of the present invention are electronically similar to P3HT.

In a first aspect, the present invention relates to a compound represented by the structural formula (I)

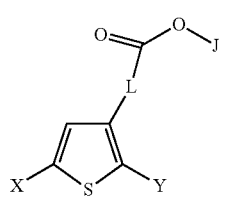

wherein:
L is a linear or branched alkylene group having from 1 to 10 carbon atoms;
J is a hydrogen atom or a linear or branched alkyl group having from 1 to 4 carbon atoms; and
X and Y are independently selected from the group consisting of hydrogen, chloro, bromo, iodo, pseudo-halogens, boronic acid, boronic esters and organotin.

This compound is a monomer suitable for being incorporated as a repeat unit or an end group in a polymer or a copolymer. At least one of functions X and Y is such to permit such incorporation.

When both X and Y are hydrogen atoms, a polymerization or copolymerization of this compound can operate via oxidative coupling.

When only one of X and Y is a hydrogen atom, incorporation can only lead to the incorporation of this compound as an end-group at the end of polymer or copolymer chains. This holds true whether the polymerization is oxidative or reductive.

When none of X and Y is hydrogen, a polymerization or copolymerization of this compound can operate via reductive coupling.

In a preferred embodiment of the present invention, the compound of the first aspect of the present invention may be polymerized or copolymerized via a reductive coupling reaction such as, but not limited to, Rieke coupling (e.g. following a procedure analog to the one disclosed in T-A. Chen, R. D. Rieke, *J. Am. Chem. Soc.* (1992) 114, 10087), McCullough coupling (e.g. following a procedure analog to the one disclosed in R. D. McCullough et al., *J. Chem. Soc., Chem. Commun.,* 1992. 70 or U.S. Pat. No. 6,166,172), Stille coupling (e.g. following a procedure analog to the one disclosed in Milstein, D.; Stille, J. K. *J. Am. Chem. Soc.* 1978, 100, 3636 or D. Milstein, J. K Stille, *J. Am. Chem. Soc.,* 1979, 101, 4992.), Suzuki coupling (e.g. following a procedure analog to the one disclosed in N. Miyaura, T Yanagi, A. Suzuki, *Synth. Commun.,* 1981, 11, 513) or Yamamoto coupling (e.g. following a procedure analog to the one disclosed in T Yamamoto, A. Morita, Y. Miyazaki, T Maruyama, H. Wakayama, Z. H. Zhou, Y. Nakamura, T Kanbara, S. Sasaki and K. Kubota, *Macromolecules,* 1992, 25, 1214).

Reductive coupling is advantageous because it permits the synthesis of regioregular polymers, i.e. polymers with a regioregularity of 80% or more, preferably 85% or more and more preferably 89% or more.

In an embodiment, the monomer may comprise two identical (i.e. X=Y) or different reactive halogens (e.g. I, Br or Cl) or pseudo-halogen. This has the effect of permitting its polymerization or co-polymerization in a Rieke or Yamamoto coupling polymerization, or its co-polymerization in a Suzuki coupling with a co-monomer comprising two identical or different reactive groups selected from the group consisting of boronic acid and boronic esters, or its co-polymerization in a Stille coupling with a co-monomer comprising two identical or different organotin reactive groups. Preferably, X=Y and most preferably X=Y=halogen.

In another embodiment, the monomer may comprise two identical or different reactive groups selected from the group consisting of boronic acid and boronic esters (preferably X=Y). This has the effect of permitting its co-polymerization in a Suzuki coupling with a co-monomer comprising two identical (i.e. X=Y) or different reactive halogens (e.g. I, Br or Cl) or pseudo-halogens.

In yet another embodiment, the monomer may comprise one reactive halogen (e.g. I, Br or Cl) or pseudo-halogen and another reactive group (i.e. X and Y are different) selected from the group consisting of boronic acid or boronic esters. This has the effect of permitting its polymerization or co-polymerization via a Suzuki coupling.

When a Suzuki coupling is performed between one co-monomer comprising two identical or different halogens or pseudo-halogens and a second co-monomer comprising two identical or different reactive groups selected from the group consisting of boronic acid and boronic esters, both co-monomers are preferably present in equimolar proportions.

In another embodiment, the monomer may comprise one reactive halogen (e.g. I, Br or Cl) or pseudo-halogen and one reactive organotin group (i.e. X and Y are different). This has the effect of permitting its polymerization or co-polymerization via a Stille coupling When a Stille coupling is performed between one co-monomer comprising two identical or different halogens or pseudo-halogens and a second co-monomer comprising two identical or different reactive organotin groups, both co-monomers are preferably present in equimolar proportions.

The nature of the end groups resulting from any of the polymerization processes above is usually difficult to determine in view of the large molecular mass of the polymer produced but it is generally accepted that they are either of the same nature as one of the leaving groups present on the starting monomer (e.g. halogen, pseudo-halogen, boronic acid, boronic ester or organotin) or hydrogen.

Methods to introduce alternative end-groups into the (co) polymer are well known to the person skilled in the art. A first method (a so-called "one pot" method) involves the addition of ending molecules together with the monomer or co-monomers into the reaction mixture right from the start of the polymerization. A second method involves a first step of producing the (co)polymer as described in the previous paragraphs, and a second step of reacting this (co)polymer with the ending molecules. In both methods the ending molecules are aromatic molecules and preferably comprise only one reactive halogen (e.g. I, Br or Cl), boronic acid, boronic ester, organotin or other group known by the person skilled in the art be useful in reductive coupling and are otherwise analog to the co-monomers described above.

An example of end-group introduction according to the first method is disclosed in C. Ego et al, *J. of the Am. Chem. Soc.* 125(2) (2003), 437-443).

In formula (I), L is preferably a linear alkylene group. L preferably has from 2 to 8 carbon atoms, more preferably from 4 to 6 carbon atoms and most preferably has 5 carbon atoms. In a preferred embodiment, L is a linear alkylene group having 5 carbon atoms, i.e. a pentamethylene group.

In formula (I), J is preferably a linear alkyl group having from 1 to 3 carbon atoms, most preferably 2 carbon atoms.

In some embodiments, the monomer of the first aspect of the present invention has the following structure:

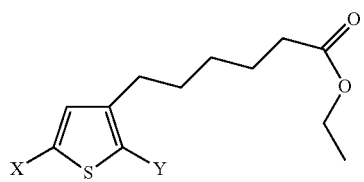

(II)

In a particular embodiment, the monomer of the first aspect of the present invention has the following structure:

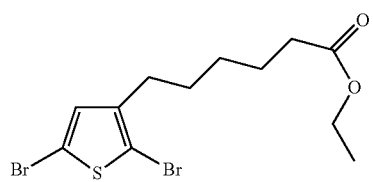

(III)

In a second aspect, the present invention relates to a polymer having at least one monomer unit according to formula (IV):

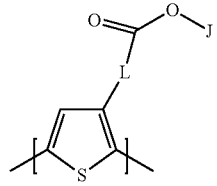

(IV)

wherein L and J are as defined in any embodiment of the first aspect of the present invention.

This polymer can be a homopolymer or a copolymer.

The weight average molecular weight Mw (measured against a polystyrene standard) of the polymer (homo- or copolymer) of this invention may be for instance in the range from about 10,000 to about 300,000 Dalton, e.g. from about 12,500 to 200,000 Dalton or from 15,000 to 100,000 Dalton.

The polydispersity index (PD=Mw/Mn) of the polymer or copolymer of this invention may for instance be comprised between 1.05 and about 10.0, e.g. between 1.5 and 5.0 or between 1.7 and 3.0, preferably from 1.8 to 2.5.

In a particular embodiment of the invention, the polymers according to the second aspect of this invention include homopolymers comprising monomer units represented by the structural formula (IV), and copolymers comprising two or more different monomer units, including at least one co-monomer Ar in addition to the monomer unit (IV), in a random, alternating or block arrangement. A random arrangement can be obtained for instance if a first and a second co-monomer can react with each other and with themselves (e.g. Yamamoto reaction). An alternating arrangement can be obtained for instance if a first and a second co-monomer can only react with each other but not with themselves (e.g. Suzuki reaction when the first monomer comprises two bromine functions and the second monomer comprises two boronic ester functions). A block arrangement can be obtained if a first co-monomer able to react with itself is allowed to polymerize for some time before a second monomer able to react with itself and with the first monomer is introduced in the reaction medium. Another way to obtain a block arrangement can be to first synthesize a polymer comprising only monomers of a first type, followed by the reaction of this polymer with another polymer comprising only monomers of a second type.

Suitable monomers that can be co-polymerized with the monomers according to any embodiments of the first aspect of the present invention, especially as represented by the structural formula (I), include monomers of the following general formula:

$$X'—Ar—Y' \quad (V)$$

wherein X' and Y' are independently selected from the group consisting of hydrogen, chloro, bromo, iodo, pseudo-halogens, boronic acid, boronic esters and organotin.

This compound (V) is a co-monomer suitable for being incorporated in a copolymer. At least one of functions X' and Y' is such as to permitting such incorporation either via copolymerization or as end groups.

When both X' and Y' are hydrogen atoms, a copolymerization of this compound can operate via oxidative coupling.

When only one of X' or Y' is a hydrogen atom, incorporation can only lead to the incorporation of this compound as an end-group at the end of polymer or copolymer chains. This holds true whether the polymerization is oxidative or reductive.

When none of X' and Y' is hydrogen, a copolymerization of this compound can operate via reductive coupling.

In a preferred embodiment of the present invention, the compound of the first aspect of the present invention may be copolymerized via a reductive coupling reaction such as mentioned above with a co-monomer of formula (V).

In preferred embodiments, the comonomer may comprise two reactive groups selected from the group consisting of halogen (e.g. I, Br or Cl), pseudo halogens, boronic acid, boronic esters, organotin, and other groups known by the person skilled in the art be useful in reductive coupling reactions. Co-monomers suitable for the formation of co-polymers according to the second aspect of the present invention includes monomers such as among others fluorene derivatives (such as but not limited to 2,7-dibromo-9,9-dialkylfluorene or 2,7-dibromo-9,9-diarylfluorenes (see e.g. C. Ego et al, *Adv. Mater.* 14 (2002) 809-811)), indenofluorene derivatives (see e.g. S. Setayesh, *Macromolecules* (2000)33:2016), phenylene or ladder-type phenylene derivatives (see e.g. J. Grimme et al., *Adv. Mat.* (1995) 7, 292), aniline derivatives, thiophene derivatives (such as 2,5-dibromothiophenes and 2,5-dibromo-3-$C_{1-20}$ alkylthiophenes), fluorenone derivatives (such as but not limited to 2,7-dibromoflurenone), naphthalene derivatives (such as but not limited to 2,6-dibromonaphthalene and 1,4-dibromonaphthalene); anthracene derivatives (such as but not limited to 1,4-dibromoanthracene, 2,6-dibromoanthracene and 9,10-dibromoanthracene); furane derivatives (such as, but not limited to, 2,5-dibromofurane); pyrrole derivatives such as, but not limited to, 2,5-dibromopyrrole); 1,3,4-oxadiazole-2,5-dyil derivatives; 1,3,4-thiadiazole-2,5-diyl derivatives; 2,3-benzo[c]thienylene derivatives; thieno[3,2-b]thiophene-2,5-diyl derivatives; pyrrolo[3,2-b]pyrrole-2,5-diyl derivatives; pyrene derivatives such as, but not limited to, 2,7-dibromopyrene and 2,7-dibromo-4,5,9,10-tetrahydropyrene; 4,4'-biphenylene derivatives; phenanthrene derivatives (such as, but not limited to, 2,7-dibromo phenanthrene; 3,6-dibromophenanthrene and 2,7-dibromo,-9,10-dihydrophenantrene); dibenzo-furane-2,7-diyl derivatives; dibenzo-thiophene-2,7-diyl derivatives, 3,6-dibromocarbazole derivatives and perylene derivatives (see C. Ego et al, *J. Am. Chem. Soc.* 125(2) (2003) 437-443).

In an embodiment, the co-monomer X'—Ar—Y' may comprise two identical (i.e. X'=Y') or different reactive halogens (e.g. I, Br or Cl) or pseudo-halogen. This has the effect of permitting its co-polymerization in a Rieke or Yamamoto coupling with a monomer according to formula (I) wherein X and Y are also halogens or pseudo halogens. It also permits its co-polymerization in a Suzuki coupling with a monomer according to formula (I) comprising two identical or different reactive groups selected from the group consisting of boronic acid and boronic esters, or its co-polymerization in a Stille coupling with a monomer according to formula (I) comprising two identical or different organotin reactive groups. Preferably, X'=Y'.

In another embodiment, the co-monomer may comprise two identical or different reactive groups selected from the group consisting of boronic acid and boronic esters (preferably X'=Y'). This has the effect of permitting its co-polymerization in a Suzuki coupling with a monomer according to formula (I) comprising two identical (i.e. X=Y) or different reactive halogens (e.g. I, Br or Cl) or pseudo-halogen.

In yet another embodiment, the co-monomer may comprise one reactive halogen (e.g. I, Br or Cl) or pseudo-halogen and another reactive group (i.e. X' and Y' are different) selected from the group consisting of boronic acid or boronic esters. This has the effect of permitting its co-polymerization in a Suzuki coupling with a monomer according to formula (I) comprising one reactive halogen (e.g. I, Br or Cl) or pseudo-halogen and another reactive group (i.e. X and Y are different) selected from the group consisting of boronic acid or boronic esters.

In another embodiment, the co-monomer may comprise one reactive halogen (e.g. I, Br or Cl) or pseudo-halogen and one reactive organotin group (i.e. X' and Y' are different). This has the effect of permitting its co-polymerization in a Stille coupling with a monomer according to formula (I) comprising one reactive halogen (e.g. I, Br or Cl) or pseudo-halogen and one reactive organotin group (i.e. X and Y are different).

In embodiments of the second aspect, the polymer may be a random, alternating or block co-polymer comprising monomer units according to formula (IV) and at least a comonomer.

In embodiments of the second aspect, said at least one comonomer is a homocyclic or heterocyclic aromatic group. This aromatic group can be substituted. For instance it can be substituted with one or more substituents independently selected from the group consisting of $C_{1-20}$-alkyl, $C_{1-20}$-alkoxy, $C_{1-20}$-alkylsulfate, phenyl and benzyl.

In other words, in embodiments of the second aspect of the present invention, the polymer may be a copolymer (e.g. a random copolymer) having a constituent unit comprising:

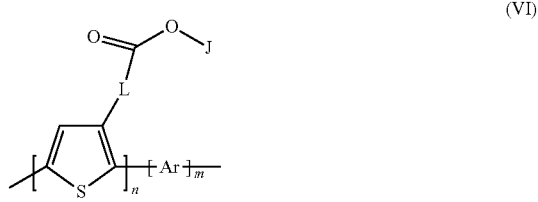

(VI)

wherein:

Ar is a homocyclic or heterocyclic aromatic group. This group can be substituted. For instance it can be substituted with one or more substituents independently selected from the group consisting of $C_{1-20}$-alkyl, $C_{1-20}$-alkoxy, $C_{1-20}$-alkylsulfate, phenyl and benzyl, m and n are the number of repeat unit, and L and J are as defined in the first aspect of the present invention.

Preferably Ar is substituted with one or more linear or branched alkyl groups having 6 to 10 carbon atoms.

In embodiments of the second aspect of the present invention, the comonomer may be according to the following formula:

(VII)

wherein R is a linear or branched alkyl group having from 6 to 10 carbon atoms.

In other words, another embodiment of the second aspect of the present invention relates to a copolymer according to the following formula:

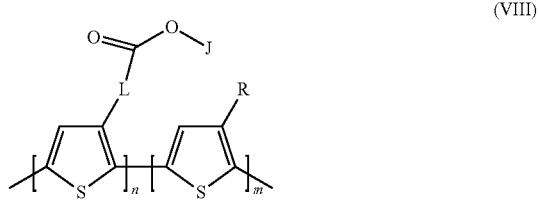

(VIII)

wherein R is a linear or branched alkyl group having from 6 to 10 carbon atoms.

In any of the embodiments of the second aspect of the present invention, the copolymer may have monomer units according to formula IV and comonomers in a ratio of from 3:2 to 1:49, preferably from 3:2 to 1:19, more preferably from 1:4 to 1:19.

In other words, in any of the embodiments of the second aspect of the present invention, m/(m+n) may be 0.40 or more, 0.60 or more or 0.80 or more. Also, in any embodiment of the second aspect of the present invention the m/(m+n) ratio can be 0.98 or less or 0.95 or less. Any of these higher limit for the m/(m+n) ratio can be combined with any of the lower limit mentioned above. For instance, the m/(m+n) ratio can be from 0.40 to 0.98 (this correspond to a m/n ratio of from 0.67 to 49), preferably m/(m+n) is from 0.40 to 0.95, more preferably from 0.80 to 0.98 or from 0.80 to 0.95. These last two range of higher (m/m+n) values are advantageous because they enable the desired increased stability without decreasing significantly the electronic properties and hence the device performance characteristics.

In a third aspect, the present invention relates to a method for producing a polymer according to the second aspect of the present invention, comprising polymerizing by reductive coupling a compound according to the first aspect and optionally a co-monomer of formula (V).

In a fourth aspect, the present invention relates to a blend for use in a photovoltaic device, comprising:
(a) a polymer having a monomer unit comprising:

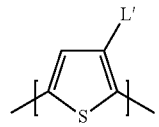
(IX)

wherein L' is selected from the group consisting of L-C(O)O-J, L-C(O)NR'-J, L-OCO-J', L-NR'CO-J', L-SCO-J', L-O-J, L-S-J, L-Se-J, L-NR'-J and L-CN, wherein L is a linear or branched alkylene group having from 1 to 10 carbon atoms, wherein J is a hydrogen atom or a linear or branched alkyl group having from 1 to 4 carbon atoms, wherein J' is a group having from 1 to 10 carbon atoms, being saturated or unsaturated, linear or branched, comprising a phenyl unit or not comprising a phenyl unit, wherein R' is a hydrogen atom or a linear or branched alkyl group having from 1 to 4 carbon atoms, and (b) an electron acceptor such as a fullerene derivative.

Fullerene derivatives include for instance $C_{28}$, $C_{36}$, $C_{50}$, $C_{60}$, $C_{70}$, $C_{72}$, $C_{76}$ and $C_{84}$ derivatives. The most commonly used fullerene derivatives are $C_{60}$ and $C_{70}$ derivatives. An example is [6,6]-phenyl-$C_{61}$-butyric acid methyl ester (PCBM) which is a $C_{60}$ derivative. Polymers incorporating fullerene units (e.g. as pendant groups) are also to be understood as being fullerene derivatives.

The blend is preferably a bulk heterojunction.

L is preferably a linear alkylene group. L preferably has from 2 to 8 carbon atoms.

In an embodiment, where L' has the formula L-C(O)O-J or L-C(O)NR'-J, L has more preferably from 4 to 6 carbon atoms and most preferably has 5 carbon atoms.

In a preferred embodiment, where L' has the formula L-C(O)O-J or L-C(O)NR'-J, L is a linear alkylene group having 5 carbon atoms, i.e. a pentamethylene group.

In an embodiment, where L' has the formula L-C(O)O-J or L-C(O)NR'-J, J is preferably a linear alkyl group having from 1 to 3 carbon atoms, most preferably 2 carbon atoms.

In some embodiments, L' has the following structure:

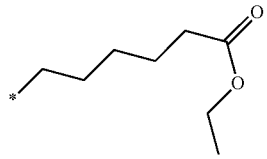 [SMILES: *CCCCCC(=O)OCC]

wherein the star indicates the attachment point to the thiophenylene.

In an embodiment, where L' has the formula L-OCO-J' or L-NR'CO-J', L has preferably from 1 to 4 carbon atoms, more preferably from 1 to 3 carbon atoms and most preferably 2 carbon atoms (i.e. is an ethylene group).

In an embodiment, where L' has the formula L-OCO-J' L-NR'CO-J', J' has preferably from 1 to 8 carbon atoms. For instance, J' can be a methyl group or a cinnamoyl group.

In an embodiment, where L' is of the formula L-O-J, L-S-J or L-Se-J, L has preferably from 1 to 4 carbon atoms, more preferably from 1 to 3 carbon atoms and most preferably 2 carbon atoms (i.e. is an ethylene group).

In an embodiment, where L' is of the formula L-O-J, L-S-J or L-Se-J, J is preferably a hydrogen or a methyl and most preferably a hydrogen.

In embodiments of the fourth aspect, the present invention relates to a blend wherein the polymer may be a random, alternating or block co-polymer comprising monomer units according to formula (IV) and at least a comonomer.

In embodiments of the fourth aspect, the at least one comonomer may be a homocyclic or heterocyclic aromatic group. This comonomer can be substituted. For instance it can be substituted with one or more substituents independently selected from the group consisting of $C_{1-20}$-alkyl, $C_{1-20}$-alkoxy, $C_{1-20}$-alkylsulfate, phenyl and benzyl.

In other words, in an embodiment, the polymer may be a copolymer according to the following formula:

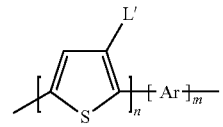
(X)

wherein:
Ar is a homocyclic or heterocyclic aromatic group. This group can be substituted. For instance it can be substituted with one or more substituents independently selected from the group consisting of $C_{1-20}$-alkyl, $C_{1-20}$-alkoxy, $C_{1-20}$-alkylsulfate, phenyl and benzyl, and m and n are the number of repeat units.

In embodiments of the fourth aspect, the present invention relates to a blend wherein said comonomer is according to the following formula:

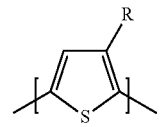
(VII)

wherein R is a linear or branched alkyl group having from 6 to 10 carbon atoms.

In other words, in another embodiment, the polymer may be a copolymer according to the following formula:

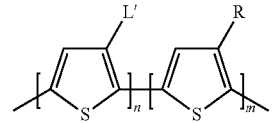
(XI)

wherein R is a linear or branched alkyl group having from 6 to 10 carbon atoms.

In embodiments, the copolymer may have monomer units according to formula IV and comonomers in a ratio of from 3:2 to 1:19, preferably from 1:4 to 1:19.

In other words, in embodiments, m/(m+n) may be from 0.40 to 0.98, preferably form 0.80 to 0.98, more preferably from 0.80 to 0.95.

In any embodiments above, the polymer may be a random copolymer, an alternating copolymer or a block copolymer.

In embodiments of the fourth aspect of the present invention, the polymer entering said blend is according to any embodiment of the second aspect of the present invention.

In a fifth aspect, the present invention relates to an opto-electronic device comprising a blend according to any embodiment of the fourth aspect of the present invention.

In order to be used as active layers, the polymers and blends according to the invention are generally applied in the form of a thin film to a substrate by known methods familiar to the person skilled in the art, such as dipping, spin coating, inkjet printing, screen printing, etc. Preferably, spin coating is used.

The invention likewise relates to organic solar cells having one or more active layers, where at least one of these active layers comprises one or more polymers or blends according to the invention.

In an embodiment, the opto-electronic device according to the fifth aspect is a photovoltaic device comprising an anode, a cathode and a blend according to the fourth aspect of the present invention wherein at least one of said anode or cathode is transparent to at least a portion of the solar spectrum. Preferably, the blend is sandwiched between said anode and said cathode.

Organic solar cells with active layers containing a polymer or a blend according the invention are fabricated using state-of-the-art procedures as described in literature (especially relating to parameters such as substrates, electrodes, p-type/n-type ratios, solvents, concentration, etc).

A typical organic photovoltaic device generally comprises:
  a substrate (preferably a transparent substrate such as glass),
  a first conductive layer (preferably a transparent conductive layer such as ITO),
  optionally, one or more hole transport layers,
  an active layer such as a blend according to an embodiment of the present invention,
  optionally, one or more electron transport layers, and
  a second conducting layer such as a metal electrode.

In embodiments of the present invention, the substrate can be formed of one material or of more than one material. The substrate can be organic or inorganic, planar or non-planar. Examples of suitable inorganic substrates are glass and quartz. Examples of suitable organic substrates are transparent polymers such as but not limited to poly(methylmethacrylate) (PMMA) and polycarbonate. The substrate can be rigid or flexible.

The first conductive layer plays the role of an anode. A typical example is indium-tin oxide (ITO). Other examples are tin oxides doped with e.g. Sn or F.

Usable materials for hole transport layers are well known to the person skilled in the art and include for instance polyaniline ("PANI"), poly(3,4-ethylenedioxythiophene) ("PEDOT"), PEDOT:PSS, polypyrrole, organic charge transfer compounds (such as e.g. tetrathiafulvalene tetracyanoquinodimethane ("TTF-TCNQ")), as well as high work function metal oxides such as molybdenum oxide, vanadium oxide, and tungsten oxide, amongst others. Another example of hole transport material is 4,4'-bis[N-(1-naphthyl)-N-phenylamino]biphenyl (α-NPD).

Usable materials for electron transport layer are well known to the person skilled in the art and include for instance a metal-chelated oxinoid compound (e.g., Alq3 or aluminum (III)bis(2-methyl-8-quinolinato)4-phenylphenolate ("BAlq")); a phenanthroline-based compound (e.g., 2,9-dimethyl-4,7-diphenyl-1,10-phenanthroline ("DDPA") or 9,10-diphenylanthracence ("DPA")); an azole compound (e.g., 2-tert-butylphenyl-5-biphenyl-1,3,4-oxadiazole ("PBD") or 3-(4-biphenyl)-4-phenyl-5-(4-t-butylphenyl)-1,2,4-triazole ("TAZ"); a diphenylanthracene derivative; a dinaphthylanthracene derivative; 4,4-bis(2,2-diphenyl-ethen-1-yl)-biphenyl ("DPVBI"); 9,10-di-beta-naphthylanthracene; 9,10-di-(naphenthyl)anthracene; 9,10-di-(2-naphthyl)anthracene ("ADN"); 4,4'-bis(carbazol-9-yl)biphenyl ("CBP"); 9,10-bis-[4-(2,2-diphenylvinyl)-phenyl]-anthracene ("BD-PVPA"); anthracene, N-arylbenzimidazoles (such as "TPBI"); 1,4-bis[2-(9-ethyl-3-carbazoyl)vinylenyl]benzene; 4,4'-bis[2-(9-ethyl-3-carbazoyl)vinylenyl]-1,1'-biphenyl; 9,10-bis[2,2-(9,9-fluorenylene)vinylenyl]anthracene; 1,4-bis[2,2-(9,9-fluorenylene)vinylenyl]benzene; 4,4'-bis[2,2-(9,9-fluorenylene)vinylenyl]-1,1'-biphenyl; perylene, substituted perylenes; tetra-tert-butylperylene ("TBPe"); bis(3,5-difluoro-2-(2-pyridyl)phenyl-(2-carboxypyridyl)iridium III ("F(Ir)Pic"), a pyrene, a substituted pyrene; a styrylamine; a fluorinated phenylene; oxidazole; 1,8-naphthalimide; a polyquinoline; one or more carbon nanotubes within PPV, as well as low work function metal oxides such as titanium oxide and zinc oxide, amongst others.

The active layer is preferably subject to an annealing step at a temperature dependent upon the copolymer ratio used in the copolymer, before the top electrode is applied. The choice of top electrode (cathode), e.g. 20 nm Ca and 80 nm Al or 100 nm Ytterbium, has little effect upon the ageing characteristics of the solar cell, but affects the absolute value of the initial power efficiency.

The invention likewise relates to organic solar cells having one or more active layers, where at least one of these active layers is made from a blend according to the fourth aspect of the present invention having one type of electronic conductivity and a second semi-conducting material (e.g. small molecule such as for example $C_{60}$ derivatives or polymers such as n-type (electron accepting) semi-conducting).

Polymers and blends according to the invention are furthermore suitable for organic based devices, for example but not limited to photovoltaic cells (bi-layers, bulk heterojunction, tandem cells, dye-sensitized, organic/organic, organic/polymer, organic/inorganic, reversed device structure, etc).

According to an embodiment of the fifth aspect of the present invention there is provided a time-stable organic solar cell comprising one or more "stable" active layer. No curing and especially no UV curing of the active layer is required to assure said stability.

In a sixth aspect, the present invention relates to the use of a polymer having a monomer unit of formula (IX) wherein L' is as defined in any embodiment of the fourth aspect of the present invention for stabilizing the morphology of a bulk-heterojunction photovoltaic cell.

DETAILED DESCRIPTION OF THE EMBODIMENTS

Definitions

Figure 1:
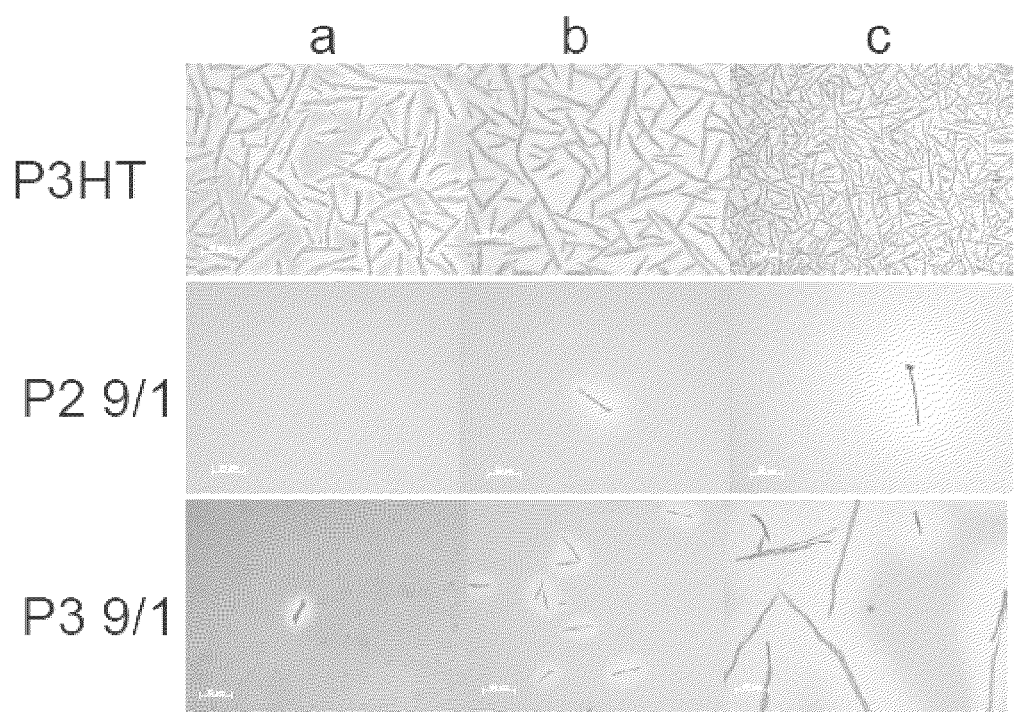
FIG. 1 shows optical micrographs of a P3HT:PCBM 1:1 blend (top, comparative), a P2 9/1:PCBM 1:1 blend (middle, embodiment) and a P3 9/1:PCBM 1:1 blend (bottom, embodiment) annealed at 125° C. for a) 15 min, b) 2 h, and c) 24 h.

As used herein and unless provided otherwise, the term "electron donor" refers to a compound capable of donating one or more electrons to an electron acceptor. Similarly, the term "electron acceptor" refers to a compound capable of accepting one or more electrons from an electron donor. Well-known electron acceptor materials are fullerenes and/or fullerene derivatives. However, other materials like, for example, cyano-substituted conjugated polymers (e.g. CN-MEH-PPV (poly-[2-methoxy-5-(2'-ethylhexyloxy)-1,4-(1-cyanovinylene)-phenylene])), benzothiadiazole-comprising conjugated polymers (e.g. F8TB (poly(9,9'-dioctlyfluoreneco-benzothiadiazole)) or perylene based small molecules (e.g. perylene dicarboxylmide derivatives) are also considered as electron acceptors. In an embodiment, the electron acceptor may be a fullerene derivative, such as [6,6]-phenyl-$C_{61}$-butyric acid methyl ester.

As used herein, and unless otherwise stated, the term "boronic ester" refers to a boronic acid derivative wherein hydrogen is replaced by any organic residue, preferably a hydrocarbyl group, and which can be obtained by condensation with alcohols or diols, including but not limited to dioxaborolanes and dioxaborinanes.

As used herein, and unless otherwise stated, the term "organotin" refers to a group represented by the structural formula $SnR_9R_{10}R_{11}$ wherein each of $R_9$, $R_{10}$ and $R_{11}$ is independently selected from the group consisting of halogen, $C_{1-20}$ alkyl, $C_{3-10}$ cycloalkyl, aryl, benzyl and $C_{2-7}$ alkenyl, provided that $R_9$, $R_{10}$ and $R_{11}$ are not simultaneously halogen; such organotin groups may be derived from tin compounds including, but not limited to, di-n-butyltin dibromide, di-n-butyltin dichloride, di-tert-butyltin dichloride, dimethyltin dibromide, dimethyltin dichloride, dimethyltin difluoride, dimethyltin diiodide, diphenyltin dichloride, diphenyltin dibromide, diphenyltin difluoride, diphenyltin diiodide, tributyltin fluoride, tributyltin chloride, tributyltin bromide, tributyltin iodide, phenyltin tribromide, phenyltin trichloride, tricyclohexyltin chloride, triethyltin bromide, triethyltin chloride, triethyltin iodide, vinyltributyltin, tetrabutyltin, butyltin trichloride, n-butylvinyltin dichloride, diallyldibutyltin, diallyldiphenyltin, dibutylvinyltin bromide, dibutylvinyltin chloride, dichlorodi-m-tolylstannane, diethyldiisoamyltin, diethyldiisobutyltin, diethyldiphenyltin, diethylisoamyltin bromide, diethylisoamyltin chloride, diethylisobutyltin bromide, diethyl-n-propyltin bromide, diethyl-n-propyltin chloride, diethyl-n-propyltin fluoride, diethyltin dibromide, diethyltin dichloride, diethyltin difluoride, diethyltin diiodide, diisoamyltin dibromide, diisoamyltin dichloride, diisoamyltin diiodide, diisobutyltin dichloride, diisobutyltin diiodide, diisopropyltin dichloride, diisopropyltin dibromide, dimethyldiethyltin, dimethyldiisobutyltin, dimethyldioctyltin, dimethyldivinyltin, dimethylethylpropyltin, dimethylethyltin iodide, dimethyldivinyltin, dimethylvinyltin bromide, dimethylvinyltin iodide, diphenyldivinyltin, dipropyltin difluoride, dipropyltin diiodide, dipropyltin dichloride, dipropyltin dibromide, di-o-tolyltin dichloride, di-p-tolyltin dichloride, ditriphenyl-stannylmethane, divinylbutyltin chloride, divinyltin dichloride, ethyldiisoamyltin bromide, ethyldiisobutyltin bromide, ethylmethylpropyltin iodide, ethyl-n-propyldiisoamyltin, ethylpropyltin dichloride, ethyltin tribromide, ethyltin triiodide, ethyltri-n-butyltin, ethyltri-n-propyltin, methyltin tribromide, methyltin trichloride, methyltin triiodide, methyltri-n-butyltin, methyltri-n-propyltin, phenylbenzyltin dichloride, phenyltribenzyltin, propyltin triiodide, propyltri-n-amyltin, tetra-n-amyltin, tetra-n-butyltin, tetrabenzyltin, tetracyclohexyltin, tetraethyltin, tetra-n-heptyltin, tetra-n-hexyltin, tetraisoamyltin, tetraisobutyltin, tetralauryltin, tetramethyltin, tetra-n-octyltin, tetraphenyltin, tetrapropyltin, tetra-o-tolyltin, tetra-m-tolyltin, tetra-p-tolyltin, tetravinyltin, tetra-m-xylyltin, tetra-p-xylyltin, o-tolyltin trichloride, p-tolyltin trichloride, m-tolyltrichlorostannane, triallylbutyltin, tri-n-amyltin bromide, tribenzylethyltin, tribenzyltin chloride, tribenzyltin iodide, tri-n-butyltin bromide, tri-n-butylvinyltin, triethyl-n-amyltin, triethylisoamyltin, triethylisobutyltin, triethylphenyltin, triethyl-n-propyltin, triisoamyltin bromide, triisoamyltin chloride, triisoamyltin fluoride, triisoamyltin iodide, triisobutylethyltin, triisobutylisoamyltin, triisobutyltin bromide, triisobutyltin chloride, triisobutyltin fluoride, triisobutyltin iodide, triisopropyltin bromide, triisopropyltin iodide, trimethyldecyltin, trimethyldodecyltin, trimethylethyltin, trimethyltin bromide, trimethyltin chloride, trimethyltin fluoride, trimethyltin iodide, triphenylallyltin, triphenylbenzyltin, triphenylbutyltin, triphenylethyltin, triphenylmethyltin, triphenyl-α-naphthyltin, triphenyltin bromide, triphenyltin chloride, triphenyltin fluoride, triphenyltin iodide, triphenyl-p-tolyltin, triphenyl-p-xylyltin, tri-n-propyl-n-butyltin, tri-n-propylethyltin, tri-n-propylisobutyl tin, tri-n-propyltin chloride, tri-n-propyltin fluoride, tri-n-propyltin iodide, tri-o-tolyltin bromide, tri-p-tolyltin bromide, tri-o-tolyltin chloride, tri-m-tolyltin chloride, tri-p-tolyltin chloride, tri-p-tolyltin fluoride, tri-o-tolyltin iodide, tri-p-tolyltin iodide, triphenylstannylmethane, trivinyldecyltin, trivinylhexyltin, trivinyloctyltin, trivinyltin chloride, vinyltin trichloride, tri-p-xylyltin bromide, tri-p-xylyltin chloride, tri-p-xylyltin fluoride, tri-p-xylyltin iodide and tri-m-xylyltin fluoride.

As used herein and unless provided otherwise, the term pseudo-halogen refers to a chemical group that behave like a halogen in reductive coupling reactions. For instance it can be selected from the group consisting of trifluoromethylmethanesulfonyl, para-toluenesulfonyl and methanesulfonyl.

As used herein with respect to a blend, and unless otherwise stated, the term "stable" indicates that the nano-morphology of the blend does not change substantially in time upon annealing under inert atmosphere for 15 min at 125° C. or even for 2 hours or 24 hours at this temperature.

As used herein and unless otherwise stated, the term "homocyclic aromatic" designates any mono- or polycyclic aromatic monovalent hydrocarbon group having from 6 to 15 carbon atoms such as, but not limited to, phenyl, naphthyl, anthracenyl, phenanthracyl, fluoranthenyl, chrysenyl, carbazolyl, pyrenyl, biphenylyl, terphenyl, picenyl, indenyl, biphenyl, indacenyl, tetrahydropyrenyl, benzocyclobutenyl, benzocyclooctenyl and the like, including fused benzo-$C_{4-8}$ cycloalkyl groups such as, for instance, indanyl, tetrahydronaphthyl, fluorenyl and the like. All of said groups can be optionally substituted with one or more substituents (preferably 1 to 3 substituents). In some embodiments, the substituents can be independently selected from the group consisting of halogen, $C_{1-12}$ alkyl, nitro, trifluoromethoxy, trifluoromethyl and $C_{1-12}$ alkoxy (all of such substituents being such as herein defined, including individual species and sub-groups thereof), such as, but not limited to, 4-fluorophenyl, 4-chlorophenyl, 3,4-dichlorophenyl, 2,6-dichlorophenyl, 2-fluorophenyl, 3-chlorophenyl, 3,5-dichlorophenyl, trifluoromethylphenyl, 3,4-dimethoxyphenyl, iodophenyl, and bromophenyl.

As used herein with respect to a substituting group, and unless otherwise stated, the term "$C_{1-n}$ alkyl" refers to a straight (non-branched) or branched chain saturated acyclic hydrocarbon monovalent group having from 1 to n carbon atoms such as, if n is 4, methyl, ethyl, propyl, n-butyl, 1-methyl-ethyl (isopropyl), 2-methylpropyl (isobutyl), and 1,1-dimethylethyl (tert-butyl). Similarly, the term "$C_{1-20}$ alkyl" refers to straight (non-branched) or branched chain groups having from 1 to 20 carbon atoms such as, for example, pentyl, hexyl, heptyl, octyl, nonyl, decyl, dodecyl, tetradecyl, hexadecyl, octadecyl and the like.

As used herein and unless otherwise stated, the terms "heterocyclic aromatic" means a mono- or polycyclic, polyunsaturated, aromatic hydrocarbon group having from 4 to 12 carbon atoms and including one or more heteroatoms in one or more heterocyclic rings, each of said rings having 5 or 6 atoms (and optionally further including one or more heteroatoms attached to one or more carbon atoms of said ring, for instance in the form of a carbonyl, and/or to one or more heteroatoms of said ring, for instance in the form of a N-oxide), each of said heteroatoms being independently nitrogen, oxygen or sulfur, also including groups wherein a heterocyclic ring is fused to one or more aromatic homocyclic rings for instance in the form of benzo-fused, dibenzo-fused and naphtho-fused heterocyclic groups; within this definition are included hetero aromatic groups such as, but not limited to, thienyl(-ene), pyrrolyl(-ene), pyridyl(-ene), carbazolyl(-ene) and benzothiazolyl(-ene).

As used herein and unless otherwise stated, the term "halogen" means any atom selected from the group consisting of fluorine, chlorine, bromine and iodine.

As used herein and unless otherwise stated, the term "$C_{1-n}$ alkoxy" refers to substituents wherein a carbon atom of a $C_{1-n}$ alkyl group (such as defined herein above, including subgroups thereof), is attached to an oxygen atom through a single bond, including methoxy, ethoxy, propoxy, n-butoxy, isopropoxy, sec-butoxy, and tert-butoxy.

As used herein and unless otherwise stated, the term "$C_{1-n}$ alkylsulfate" refers to substituents wherein a carbon atom of a $C_{1-n}$ alkyl group (such as defined herein above, including sub-groups thereof), is attached to an oxygen atom of a sulfate group through a single bond such as, but not limited to methylsulfate (methoxysulfonyloxy), ethylsulfate (ethoxysulfonyloxy), n-butylsulfate (n-butoxysulfonyloxy), tert-butylsulfate (tert-butoxysulfonyloxy), undecylsulfate (undecyloxysulfonyloxy), and the like.

As used herein with respect to organic devices, and unless otherwise stated, the term "active layer" designates an organic layer which includes an organic semiconductor material exhibiting one type of electronic conductivity and possibly a second semiconductor material having the same or opposite type conductivity.

General Experimental Materials and Methods

All chemicals were used as obtained from commercial sources, unless stated otherwise. THF and diethylether were distilled after drying with sodium wire and benzophenone until a blue color appeared. 3-Bromothiophene was purified using short path distillation. NMR spectra were recorded on a Varian Inova 300 spectrometer at 300 MHz for $^1$H and at 75 MHz for $^{13}$C NMR using a 5 mm probe. Deuterated CHCl$_3$ was obtained from Cambridge Isotope Laboratories, Inc. $^1$H and $^{13}$C chemical shifts were reported downfield from tetramethylsilane (TMS) using the peak of residual CHCl$_3$ as an internal standard at $\delta$=7.24 ppm. UV-Vis spectra were recorded using films dropcast from a CHCl$_3$ solution on a quartz substrate on a Varian CARY 500 UV-Vis-NIR spectrophotometer from 200 to 800 nm at 600 nm/min. Fourier transform infrared (FT-IR) was performed on a Perkin Elmer Spectrum One FT-IR spectrometer with a nominal resolution of 4 cm$^{-1}$. Samples for the FTIR were pellets in KBr or films dropcast from a CHCl$_3$ solution. Gas chromatography/mass spectrometry (GC-MS) was carried out on TSQ-70 and Voyager mass spectrometers. Size exclusion chromatography (SEC) was performed on a 1 wt % polymer solution, which was filtered with a 0.45 μm pore PTFE syringe filter. A Spectra series P100 (Spectra Physics) pump equipped with two mixed-B columns (10 μm, 2×30 cm, Polymer Labs) and a refractive index detector (Shodex) at 40° C. in THF at a flow rate of 1.0 ml/min were used. Molecular weight distributions were measured relative to polystyrene standards. Toluene was used as a flow rate marker.

For every accelerated lifetime measurement, a new substrate with 4 solar cells was used. The displayed $J_{sc}$ was the averaged $J_{sc}$ of the 4 solar cells. To obtain a continuous degradation curve, outliers were removed. The influence of a prolonged thermal treatment on the photovoltaic performance of the devices was measured in a set-up that measured Solar cell characteristics ($J_{sc}$, $V_{oc}$, FF, Eff) was measured every 30 minutes. In between the measurements, the samples were kept in the dark.

Monomer Synthesis

Synthesis of 3-Hexylthiophene (1)

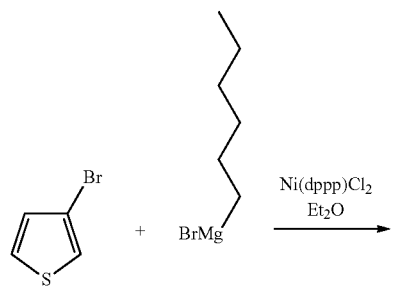

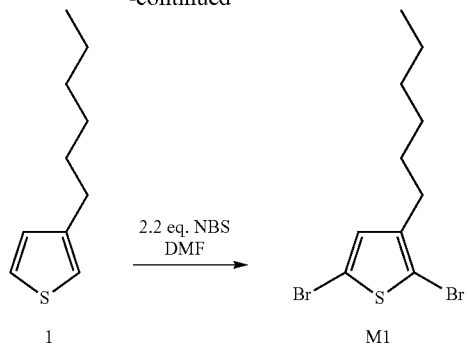

Starting from the commercially available products 3-bromothiophene (3-BT) and hexylmagnesiumbromide, 1 was produced using a Ni catalyst. In a three-necked flask, 100 ml (1 eq, 166.0 g, 1.018 mol) of bromothiophene is stirred under nitrogen atmosphere with 0.01 equivalent of Ni(dppp)Cl$_2$ (5.19 g, 0.0102 mol) and 300 ml dry diethylether. 1.2 equivalent (0.611 l of a 2.0M solution in diethyl ether, 1.22 mol) of hexylmagnesiumbromide was added dropwise at a temperature of 0° C. The reaction was stirred overnight at room temperature before neutralization by addition of a 1M HCl solution. After extraction with diethyl ether, washing with a saturated NaHCO$_3$ solution and drying over MgSO$_4$ a brown liquid was obtained. This liquid was purified by short path distillation to obtain 1 in a yield of 95.6% (163.73 g, 0.973 mol) at p=7.10$^{-3}$ mbar and T=81-84° C.

Characterization: TLC (hexane): R$_f$=0.81; $^1$H NMR (300 MHz, CDCl$_3$): $\delta$ 7.23 (s, H), 6.95 (d, H), 6.92 (d, H), 2.63 (t, CH$_2$), 1.63 (q, CH$_2$), 1.32 (m, 3CH$_2$), 0.90 (t, CH$_3$); $^{13}$C NMR (75 MHz, CDCl$_3$): $\delta$ 142.8, 130.8, 110.2, 107.2, 31.5, 29.4, 29.3, 28.7, 22.5, 14.0; GC/MS (m/z): 168 [M]$^+$, 153 [M-CH$_3$]$^+$, 139 [M-CH$_2$CH$_3$]$^+$, 125 [M-(CH$_2$)$_2$CH$_3$]$^+$, 111 [M-(CH$_2$)$_3$CH$_3$]$^+$, 97 [M-(CH$_2$)$_4$CH$_3$]$^+$, 85 [M-(CH$_2$)$_5$CH$_3$]$^+$; FT-IR: 3000-2800 cm$^{-1}$ (C—H stretch alkyl), 1600-1500 cm$^{-1}$ (C=C stretch aromatic ring).

Synthesis of 2,5-dibromo-3-hexylthiophene (M1)

M1 is an Intermediate in the Synthesis of P1, P2, P3 and P4

A solution of NBS (2.2 eq, 23.26 g, 0.130 mol) in 100 ml DMF was added dropwise to a solution of 1 (10 g, 0.059 mol) in 100 ml DMF and stirred in the dark at 0° C. When addition was complete, the reaction was allowed to warm to room temperature. After stirring for 48 h, the solution was added to 100 ml of an ice cooled 2.5M NaOH solution and stirred before extraction with 3×100 ml diethyl ether. The organic phase was washed using 100 ml of 2.5M NaOH solution, H$_2$O and NaCl$_{sat}$ and dried with MgSO$_4$ to obtain a yellow liquid that was purified using short path distillation to yield 81% (15.50 g, 0.048 mol) of a colorless liquid.

Characterization $^1$H NMR (300 MHz, CDCl$_3$): $\delta$ 6.76 (s, H), 2.49 (t, CH$_2$), 1.53 (q, CH$_2$), 1.29 (m, 3CH$_2$), 0.89 (t, CH$_3$); GC/MS (m/z): 326 [M]$^+$, 255 [M-(CH$_2$)$_4$CH$_3$]$^+$, 247 [M-Br]$^+$, 177 [M-Br, (CH$_2$)$_4$CH$_3$]$^+$, 111 [M-(CH$_2$)$_3$CH$_3$]$^+$, 95 [M-2Br, (CH$_2$)$_4$CH$_3$]$^+$. FT-IR: 3000-2800 cm$^{-1}$ (C—H stretch alkyl); 1600-1500 cm$^{-1}$ (C=C stretch aromatic ring).

2,5-dibromo-3-ethanolthiophene (2)

(2) is an Intermediate in the Synthesis of M2, P1, P2 and P3

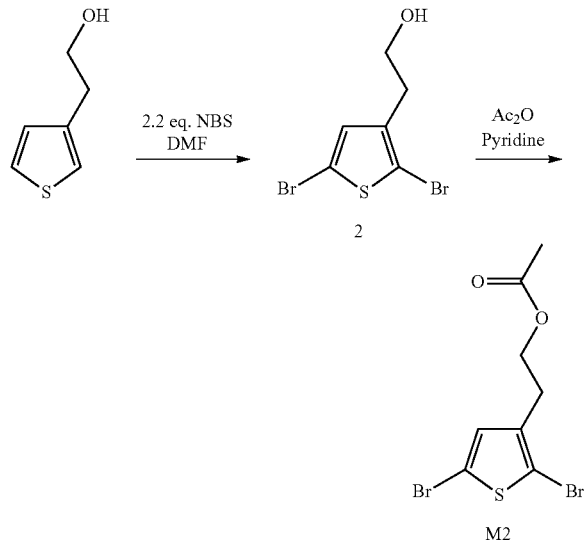

2 was obtained by dibromination of 3-ethanolthiophene using NBS in an analogous procedure to that used for M1. 2.2 eq of NBS (32.93 g, 0.185 mol) was dissolved in 100 ml DMF and added dropwise to 3-ethanolthiophene (1 eq, 10.75 g, 0.084 mol) in 100 ml DMF at 0° C. The reaction was allowed to warm to room temperature and stirred for 48 h. The solution was added to 100 ml of an ice cooled 2.5M NaOH solution and stirred before extraction with 3×100 ml diethyl ether. The organic phase was washed with 100 ml of a 2.5M NaOH solution, $H_2O$ and $NaCl_{sat}$, and dried with $MgSO_4$. The yellow liquid obtained was purified using short path distillation to isolate a colorless liquid (18.66 g, 73.5 mmol, 95%) at $p=4.10^{-3}$ mbar, T=107° C. $^1$H-NMR (300 MHz; $CDCl_3$): δ 6.82 (s, 1H), 3.72 (t, 2H), 2.73 (t, 2H), 2.52 (s, 1H); $^{13}$C-NMR (75 MHz, $CDCl_3$): δ 139.0, 131.2, 110.7, 109.3, 61.5, 32.2; GC/MS m/z 288, 286, 284 [M]$^+$ 257, 255, 253 [M-$CH_2OCH$]$^+$ 257, 255, 253 [M-$CH_2OC(O)CH_3$]$^+$ 189, 187 [M-Br, $OCOCH_3$]$^+$

2,5-dibromo-3-acetylethanolthiophene (M2). M2 is an Intermediate in the Synthesis of P1

M2 was obtained after stirring 2 (1 eq, 36.2 g, 0.143 mol) under reflux with 1.3 eq. (18.93 g, 0.185 mol) of acetic anhydride and 140 ml of pyridine for 5 hours. The mixture was neutralized by adding HCl, extracted with 3×100 ml diethyl ether and washed with 3×100 ml $H_2O$. The extract was dried over $MgSO_4$, filtered and evaporated. The mixture was purified with short path distillation to provide 36.2 g (113 mmol, 78%) of M2 at $p=1.10^{-3}$ mbar and T=95° C.

Characterization: TLC (hexane:diethyl ether, 8:2) $R_f$=0.81, $^1$H-NMR (300 MHz, $CDCl_3$): δ 6.79 (s, 1H), 4.17 (t, 2H), 2.82 (t, 2H), 2.02 (s, 3H); $^{13}$C-NMR (75 MHz, $CDCl_3$): δ 170.7, 138.1, 130.8, 110.7, 109.6, 62.8, 28.7, 20.8; GC/MS (m/z) 330, 328, 326 [M]$^+$ 270, 268, 266 [M-$OCOCH_3$]$^+$ 257, 255, 253 [M-$CH_2OC(O)CH_3$]$^+$ 205, 207 [M-Br]$^+$ 187, 189 [M-Br, $OCOCH_3$]$^+$ 176, 174 [M-Br, $CH_2OC(O)CH_3$]$^+$ 108 [M-2Br, $CH_2OC(O)CH_3$]$^+$, 95 M-2Br, $CH_2CH_2OC(O)CH_3$]$^+$ $v_{max}$(film)/cm$^{-1}$

6-(2,5-dibromo-thiophen-3-yl)-hexanoic acid ethyl ester (M3)

M3 is an Embodiment of the Present Invention and an Intermediate in the Synthesis of P4

M3 was obtained using a similar procedure as was utilized to obtain M1, starting from 6-bromoethylhexanoate and 3-bromothiophene 6-Bromo-hexanoic acid ethyl ester (20 g, 89 mmol) was added to active zinc and stirred for 2 h at room temperature under argon atmosphere. The zinc particles were allowed to settle overnight. The supernatant organozinc compound was added dropwise to a solution of 16.81 g 3-Bromothiophene (103 mmol) and 0.05 eq Ni(dppp)$Cl_2$ in THF. The reaction was stirred for 48 h at room temperature and quenched with a saturated $NH_4Cl$ solution. After extraction with $Et_2O$ (3×200 mL), the organic phase was dried over $MgSO_4$ and filtrated. 8.6 g 6-(2,5-dibromo-thiophen-3-yl)-hexanoic acid ethyl ester] (38 mmol, 42%) was obtained with short path distillation at T=72° C. and $p=1.10^{-3}$ mbar.

$^1$H NMR (300 MHz, $CDCl_3$) δ 7.20 (m, 1H, $H_{arom}$), 6.90 (m, 2H, $H_{arom}$), 4.10 (q, 2H, O—$CH_2$, J=7.5 Hz), 2.62 (t, 2H, α-$CH_2$, J=7.5 Hz), 2.28 (t, 2H, β-$CH_2$, J=7.5 Hz), 1.63 (m, 4H, 2$CH_2$), 1.38 (m, 2H, $CH_2$), 1.23 (t, 3H, $CH_3$, J=7.1 Hz);

$^{13}$C NMR (75 MHz, $CDCl_3$) δ 173.4, 142.4, 127.8, 124.8, 119.6, 59.8, 33.9, 29.8, 29.6, 28.4, 24.4, 13.8;

GC/MS 95% pure, m/z 226 [M]$^+$, 181 [M-$OCH_2CH_3$]$^+$, 153 [M-$C(O)OCH_2CH_3$]$^+$, 139 [M-$CH_2C(O)OCH_2CH_3$]$^+$, 125 [M-$(CH_2)_2C(O)OCH_2CH_3$]$^+$, 111 [M-$(CH_2)_3C(O)OCH_2CH_3$]$^+$, 97 [M-$(CH_2)_4C(O)OCH_2CH_3$]$^+$;

FT-IR (NaCl, cm$^{-1}$): 3104, 2980, 2934, 2858, 1733 (vs), 1537, 1463, 1372, 1299, 1252, 1181, 1130, 1096, 1032, 859, 833, 773

Polymer Synthesis

Synthesis of poly(3-hexyl-thiophene) (P3HT) (Comparative)

P3HT for use in a solar cell as a reference system was synthesized using the Rieke method for the production of highly regioregular poly(3-alkylthiophene)s. A solution of M1 (1 eq, 10.04 g, 0.031 mol) in 80 ml THF was added to active Zinc at −78° C. The organozinc solution formed was added to a solution of 0.002 eq (0.035 g, 6.4 10$^{-5}$ mol) Ni(dppp)$Cl_2$ in 40 ml THF and stirred under inert atmosphere at 60° C. for 18 h. The crude polymer was precipitated in a MeOH/2M HCl (2/1, v/v) mixture and purified by solid phase extraction with methanol and hexane. The purified polymer was extracted with chloroform and precipitated in MeOH before filtration and drying, yielding 3.63 g (67%) of conjugated polymer.

GPC (THF): $M_n$=27,800; $M_w$=53,500; polydispersity index, Đ=1.9;

Synthesis of random copolymers of 3-hexylthiophene (M1) and 3-(2-acetoxyethyl)thiophene (M2) (P1), random copolymers of 3-hexylthiophene and 3-hydroxyethylthiophene (P2), and random copolymers with a 9:1 molar ratio of 3-hexylthiophene and 3-cinnamoyloxyethylthiophene (P3)

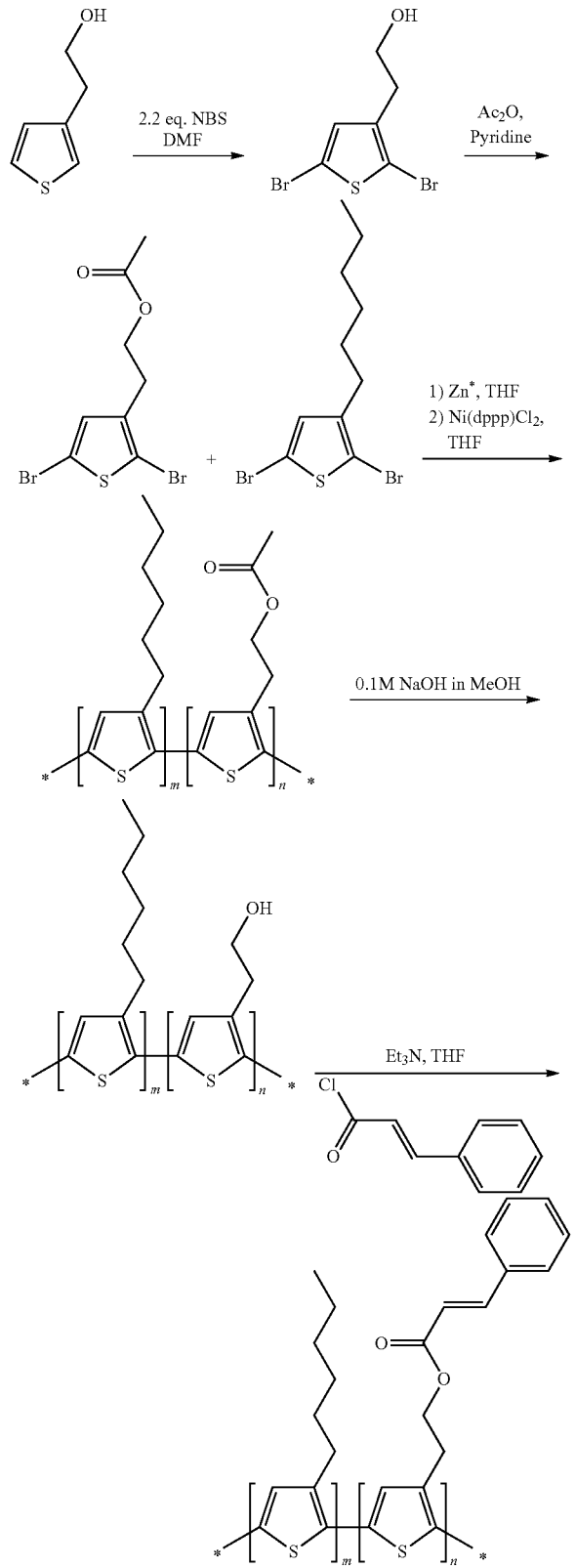

a) synthesis of poly-3-hexylthiophene-co-3-(2-acetoxyethyl)thiophene (P1 9/1)

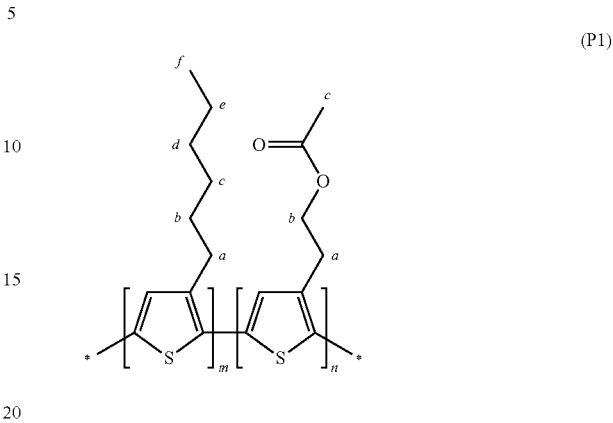

A solution of a mixture of 2,5-dibromo-3-(2-acetoxyethyl) thiophene (M2) (10% molar) (1.05 g, 0.003 mol) and 2,5-dibromo-3-hexylthiophene (M1) (90% molar) (9.41 g, 0.029 mol) in THF was added to active zinc at −78° C. to form an organozinc solution which was then polymerized in the presence of a Ni(dppp)Cl$_2$ catalyst. After reaction, the co-polymer was precipitated in a mixture of MeOH and 2M HCl (2/1). The crude co-polymer was purified using a soxhlet extraction with methanol and pentane. The purified poly-3-hexylthiophene-co-3-(2-acetoxyethyl)thiophene (P1 9/1) was extracted with chloroform and precipitated again in MeOH, before filtration and drying to obtain 3.18 g of a 9/1 copolymer in 61% yield, which was characterized as follows:

GPC (THF): $M_n$=34,400; $M_w$=65,500; polydispersity index, D=1.9;

$^1$H-NMR (CDCl$_3$): δ=7.00 (1H$_{arom,AcET}$, s), 6.96 ppm (1H$_{arom,3HT}$, s), 4.35 ppm (2H$_{b,AcET}$, t), 3.14 ppm (2H$_{a,AcET}$, t), 2.79 ppm (2H$_{a,3HT}$, t), 2.05 ppm (3H$_{c,AcET}$, s) 1.70 ppm (2H$_{b,3HT}$, t), 1.45 ppm (2H$_{c,3HT}$, m), 1.40 ppm (2H$_{d,3HT}$, m), 1.35 ppm (2H$_{e,3HT}$, m), and 0.90 ppm (3H$_{f,3HT}$, t);

UV/Vis: λmax at 555 nm; shoulder at 600 nm;
infrared spectrum: see Table 1 below.
Regioregularity: 93%

This procedure has been repeated with 30% molar M2 and 50% molar M2 to lead to polymers P1 7/3 and P1 1/1 respectively.

Mixtures of bromated monomers were made in several molar ratios (7/3, 1/1). Respectively 25 and 20 mmol (8.12 and 6.49 g) of M1 and 11 and 20 mmol (3.49 and 6.50 g) of M2 were dissolved in dry THF under Ar atmosphere. These solutions were added to active Zinc at −78° C. Solutions of 0.002 equiv Ni(dppp)Cl$_2$ in THF were added to the obtained organozinc solutions, and stirred under inert atmosphere at 60° C. for 18 h. The crude polymers were precipitated in a MeOH/2 M HCl (2/1, v/v) mixture and purified by Soxhlet extractions with methanol, hexane and acetone, subsequently. The purified polymers were extracted with chloroform and precipitated in MeOH before filtration and isolation of copolymers P1 7/3 and P1 1/1 respectively.

P1 7/3 was obtained with a Mw of 45,000, a polydispersity index D of 2.1 and a regioregularity of 93%.
Yield: 3.0 g, 52%
UV-Vis (film, λ$_{max}$, nm) 547, 595sh;
FT-IR (KBr, ν, cm$^{-1}$): 2953, 2925 and 2855 (C—H), 1743 (C=O), 1509 and 1456 (C=C), 1376 (CH$_3$), 1363, 1234, 1037, 821 (C—H)

$^1$H NMR (300 MHz, CDCl$_3$, δ): 7.05, 7.0 and 6.96 (1H, m, Th), 4.35 (2H M2, br s, β-CH$_2$), 3.10 (2H M2, br s, α-CH$_2$), 2.78 (2H, t, H-T α-CH$_2$), 2.54 (2H, br s, H—H α-CH$_2$), 2.06 (3H M2, s, CH$_3$), 1.69-1.23 (8H, m, β, γ, δ and ε-CH$_2$), 0.89 (3H, s, CH$_3$).

P1 1/1 was obtained with a Mw of 26800, a polydispersity index D of 1.5 and a regioregularity of 93%.

Yield: 2.98 g, 51%

UV-Vis λ$_{max}$ (film)/nm 547, 595sh;

FT-IR (KBr, ν, cm$^{-1}$): 3431 (br, H$_2$O), 2956, 2923 and 2853 (C—H), 1733 (C=O), 1632, 1455 (s, C=C), 1376 (CH$_3$), 1259, 1123, 1002, 867

$^1$H NMR (300 MHz, CDCl$_3$, δ): 7.11, 7.06, 7.01 and 6.96 (1H, m, Th), 4.35 (2H M2, br s, β-CH$_2$), 3.10 (2H M2, br s, α-CH$_2$), 2.79 (2H, t, H-T α-CH$_2$), 2.56 (2H, br s, H—H α-CH$_2$), 2.06 (3H M2, s, CH$_3$), 1.70-1.23 (8H, m, β, γ, δ and ε-CH$_2$), 0.89 (3H, m, CH$_3$)

The M1/M2 ratio in the monomer corresponds to the m/n ratio in the polymer.

b) synthesis of poly-3-hexylthiophene-co-3-(2-hydroxyethyl)thiophene (P2)

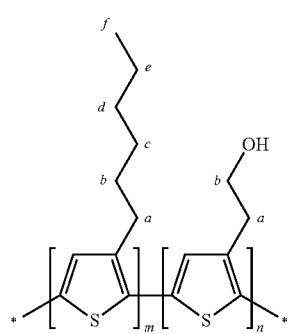

P2

1.04 g of finely grounded copolymer P1 9/1 was refluxed under an inert atmosphere with 100 mL of 0.2 M NaOH solution in MeOH for 24 h. The mixture was poured in 600 ml methanol/2M HCl mixture and stirred. The copolymer P2 9/1 was filtered off and rinsed with H$_2$O and MeOH to yield P2 9/1 in 98% yield, which was characterized as follows:

GPC (THF): M$_n$=31,100, M$_w$=68,100, D=2.2;

$^1$H-NMR (CDCl$_3$): δ=7.03 (1H$_{arom,ET}$, s), 6.96 ppm (1H$_{arom,3HT}$, s), 3.94 ppm (2H$_{b,ET}$, t), 3.09 ppm (2H$_{a,ET}$, t), 2.79 ppm (2H$_{a,3HT}$, t), 1.70 ppm (2H$_{b,3HT}$, t), 1.45 ppm (2H$_{c,3HT}$, m), 1.40 ppm (2H$_{d,3HT}$, m), 1.25 ppm (2H$_{e,3HT}$, m), and 0.90 ppm (3H$_{f,3HT}$, t);

UV/Vis (film): λmax at 551 nm, shoulder at 600 nm;

FT-IR (KBr, cm$^{-1}$): 2953 and 2853 (C—H), 1640, 1508 and 1455 (C=C), 1376 (CH$_3$), 1292-1046 and 821 cm$^{-1}$ (C—H), 723 (CH$_3$). See also Table 1 below.

Regioregularity: 93%

This same procedure was repeated using 1 g of finely grounded copolymer P1 7/3 to lead to copolymers P2 7/3.

0.9 g of P2 7/3 was obtained in 95% yield, which was characterized as follows:

GPC (THF): M$_n$=21 500, M$_w$=42 100, D=2.0;

FT-IR (KBr, cm$^{-1}$): 2951, 2923 and 2853 (C—H), 1639, 1509 and 1455 (C=C), 1376 (CH$_3$), 1290, 1132, 1042 and 821 cm$^{-1}$ (C—H) 722 (CH$_3$)

$^1$H-NMR (300 MHz, CDCl$_3$, δ): 7.05, 7.02 and 6.96 (1H, m, Th), 3.96 (2H, t, CH$_2$—OH), 3.10 (2H, t, α-CH$_2$CH$_2$—OH), 2.78 (2H, t, H-T α-CH$_2$), 2.56 (2H, br s, H—H α-CH$_2$), 1.69-1.23 (8H, m, β, γ, δ, ε-CH$_2$), 0.90 (3H, t, CH$_3$)

Regioregularity: 93%

This same procedure was repeated using 1 g of finely grounded copolymer P1 1/1 to lead to copolymers P2 1/1.

1.0 g of P2 (1/1) was obtained in 100% yield, which was characterized as follows:

GPC (THF): M$_n$=9 500, M$_w$=17 700, D=1.9;

FT-IR (KBr, cm$^{-1}$): 2920 and 2850 (C—H), 1639, 1508 and 1455 (C=C), 1376 (CH$_3$), 1298, 1230, 1142, 1038 and 823 cm$^{-1}$ (C—H);

$^1$H-NMR (300 MHz, CDCl$_3$, δ): 7.02 and 6.96 (1H, m, Th), 3.96 (2H, t, CH$_2$—OH), 3.09 (2H, t, α-CH$_2$CH$_2$—OH), 2.78 (2H, t, H-T α-CH$_2$), 1.68-1.23 (8H, m, β, γ, δ, ε-CH$_2$), 0.90 (3H, t, CH$_3$)

Regioregularity: 93% c) synthesis of poly-co-(3-hexylthiophene-co-3-cinnamoyloxyethylthiophene (P3)

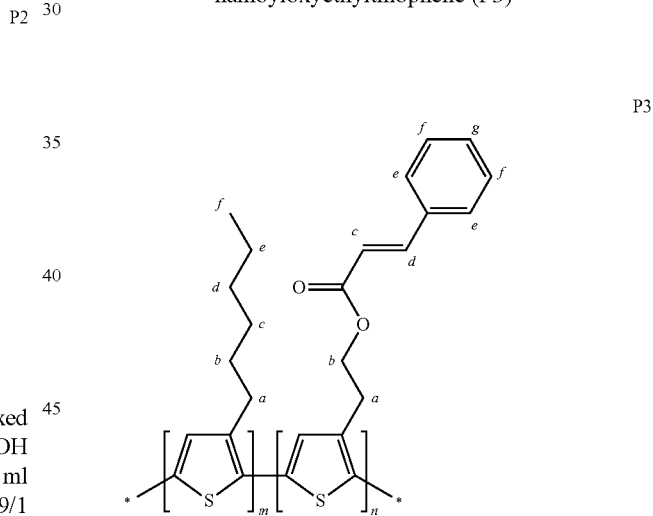

P3

0.61 g P3 9/1 was obtained in 95% yield by reacting 0.60 g poly-3-hexylthiophene-co-3-(2-hydroxyethyl)thiophene (P2 9/1) with 0.62 g (0.004 mol) cinnamoyl chloride in THF in the presence of 0.37 g (0.004 mol) triethylamine, and was purified using soxhlet extraction with methanol and acetone before characterization as follows:

GPC (THF): M$_n$=33,100, M$_w$=74,500, D=2.2;

$^1$H-NMR (300 MHz, CDCl$_3$): δ=7.67 ppm (1H$_{d,cin}$, d), 7.47 ppm (2H$_{e,cin}$, m), 7.32 ppm (2H$_{f,cin}$, m), 7.05 ppm (1H$_{g,cin}$, m), 6.96 ppm (1H$_{arom,3HT,\ and\ cin}$, s) 6.42 ppm (1H$_{c,cin}$, d), 4.49 ppm (2H$_{b,cin}$, t), 3.23 ppm (2H$_{a,cin}$, t), 2.79 ppm (2H$_{a,3HT}$, t), 1.70 ppm (2H$_{b,3HT}$, m), 1.40 ppm (2H$_{c,3HT}$, m), 1.35 ppm (2H$_{d,3HT}$, m), 1.25 ppm (2H$_{e,3HT}$, m), and 0.90 ppm (3H$_{f,3HT}$, t); and integrations originating from the M2 monomer unit corresponded to about 10% of a comparable integration originating from the M1 monomer unit, indicating that 1 out of 10 monomer units has a functionalized side chain. Disappearance of the methyl group in the acetylester of the P1 side chain at δ=2.05 ppm proved hydrolysis was completed. The complete functionalization was also illustrated by a change in chemical shift of CH$_2$-proton signals in P3 because of a different ester. Appearance of double bond and aromatic proton signals in the functionalized polymer confirmed the presence of the cinnamoyl ester in the side chain.

UV/Vis: λmax at 275 nm and 551 nm, shoulder at 600 nm. $\lambda_{max}$ at 275 nm of polymer films dropcast from chloroform solutions was due to the presence of the cinnamic acid ester in the copolymer side chain. In the absorption region of the conjugated polymer, the shoulder at 600 nm had a higher intensity, but was less sharply pronounced.

infrared spectrum: FT-IR (KBr, cm$^{-1}$): 2956, 2923, 2853, 1711, 1635, 1505, 1449, 1375, 1306, 1259, 1158, 1075, 818; see also Table 1 below.

Regioregularity: 94%

Analogous reactions were performed on P2 7/3 and P2 1/1 to give P3 7/3 and P3 1/1 respectively.

P3 7/3 was characterized as follow:

UV-Vis film ($\lambda_{max, film}$) 549 nm, shoulder at 599 nm;

GPC (THF): M$_n$=25 300, M$_w$=47 500, D=1.9; FT-IR (KBr, cm$^{-1}$):2956, 2924, 2853, 1712, 1635, 1510, 1449, 1377, 1307, 1262, 1201, 1161, 1090, 1021, 804;

$^1$H NMR (300 MHz, CDCl$_3$, δ): 7.70 and 7.64 (d, 1H, C=CH-Ph), 7.46 (m, 2H, CH$_{Ph}$), 7.33 (m, 2H, CH$_{Ph}$), 7.12-6.96 (m, H$_{Th}$ and H$_{Ph}$), 6.44 and 6.39 (d, 1H, COCH=C), 4.48 (t, 2H, CH$_2$O), 3.21 (t, 2H, α-CH$_2$), 2.77 (t, 2H, H-T α-CH$_2$ 3-HT) and 2.56 (α-CH$_2$ 3-HT), 1.67-1.31 (m, 6H, γ, δ, ε-CH$_2$ 3-HT), 0.88 (t, 3H, CH$_3$).

Regioregularity: 93%

P3 1/1 was characterized as follow:

UV-Vis ($\lambda_{max, film}$) 521;

GPC (THF): M$_n$=19 800, M$_w$=40 300, D=2.0;

FT-IR (KBr, cm$^{-1}$): 3060, 2954, 2926, 2855, 1714, 1637, 1511, 1495, 1450, 1378, 1327, 1309, 1282, 1202, 1162, 1071, 978, 862, 823, 766;

$^1$H NMR (300 MHz, CDCl$_3$, δ): 7.68 and 7.63 (d, 1H, C=CH-Ph), 7.46 (m, 2H, CH$_{Ph}$), 7.32 (m, 2H, CH$_{Ph}$), 7.12-6.96 (m, H$_{Th}$ and H$_{Ph}$), 6.43 and 6.38 (d, 1H, COCH=C), 4.47 (t, 2H, CH$_2$O), 3.21 (t, 2H, α-CH$_2$), 2.76 (t, 2H, H-T α-CH$_2$ 3-HT) and 2.56 (α-CH$_2$ 3-HT), 1.67-1.23 (m, 2H, β-CH$_2$ 3-HT), 1.30-1.23 (m, 6H, γ, δ, ε-CH$_2$ 3-HT), 0.88 (t, 3H, CH$_3$)

The C=O ester absorption at about 1740 cm$^{-1}$ in P1 disappeared upon its hydrolysis to P2. Upon functionalization of P2 to P3 a peak at around 1715 cm$^{-1}$ appeared due to the C=O bond of the cinnamic ester group.

Synthesis of Random Copolymers of 3-Hexylthiophene and 3-cinnamoylaminoethylthiophene (P14)

The synthesis proceeds according to the following scheme and provides a copolymer comprising recurrent units from a monomer represented by the structural formula (IX) wherein L' is L-NR'CO-J', L is ethylene, R' is H, and J' is cinnamoyl.

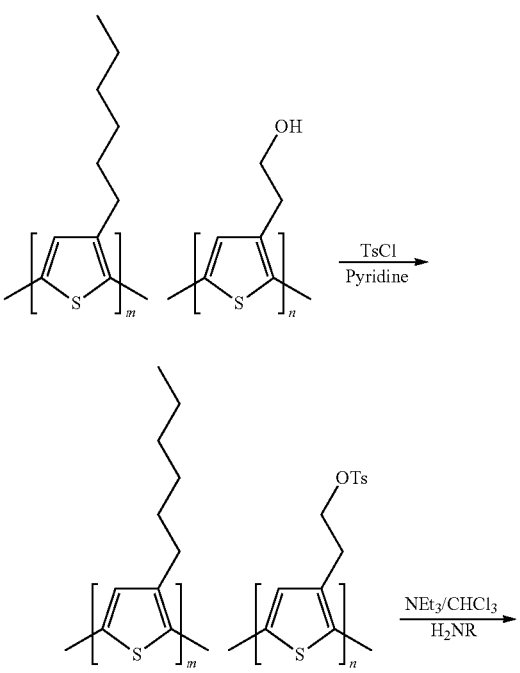

TABLE 1

| Absorption: | wavenumber (cm$^{-1}$) of absorptions observed in FT-IR | | | |
|---|---|---|---|---|
| | P3HT homopolymer | 10% ester functionalized copolymer (P1 9/1) | 10% ethanol functionalized copolymer (P2 9/1) | 10% cinnamon functionalized copolymer (P3 9/1) |
| C—H stretch on aromatic ring | 2953 | 2952 | 2952 | 2950 |
| C—H stretch in aliphatic chain | 2923 | 2922 | 2922 | 2923 |
| C—H stretch in aliphatic chain | 2853 | 2853 | 2852 | 2853 |
| C=O stretch ester bond | — | 1742 | — | 1715 |
| Conjugated system | 1635 | 1635 | 1640 | 1635 |
| C=C asymmetric ring stretch | 1508 | 1507 | 1508 | 1505 |
| C=C symmetric ring stretch | 1454 | 1452 | 1455 | 1449 |
| methyl deformation | 1376 | 1376 | 1376 | 1375 |
| C—O stretch | — | 1225 | 1262 | 1259 |
| C—H in plane bending of 2,3,5 substituted thiophene | 1088 | 1032 | 1046 | 1075 |
| C—H out of plane bending of 2,3,5 substituted thiophene or C—S stretching | 820 | 819 | 821 | 818 |
| methyl rock | 724 | 723 | 723 | 721 |

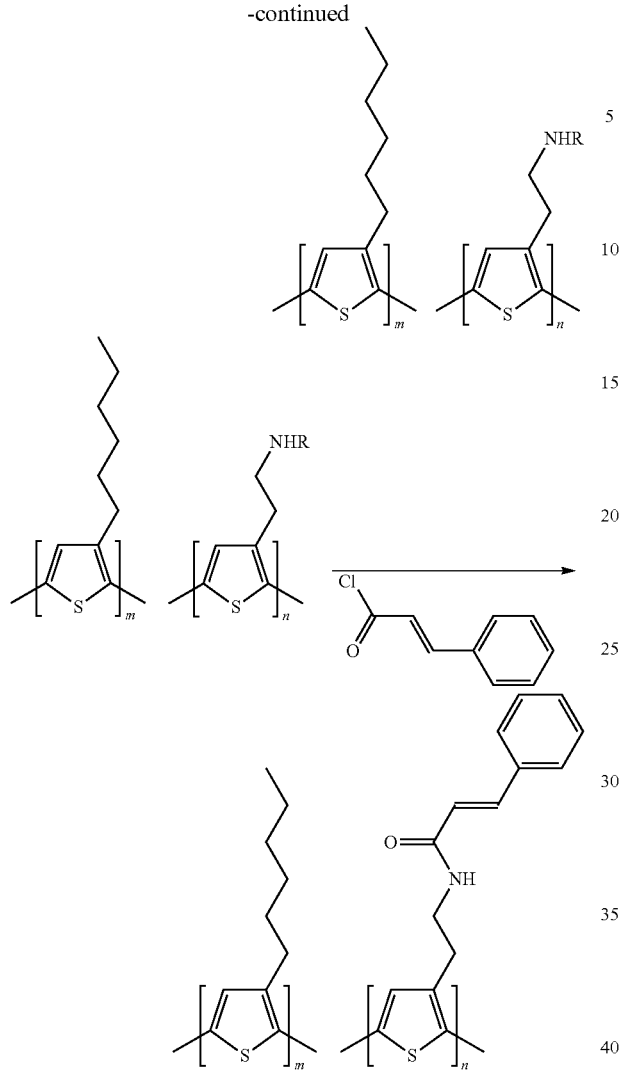
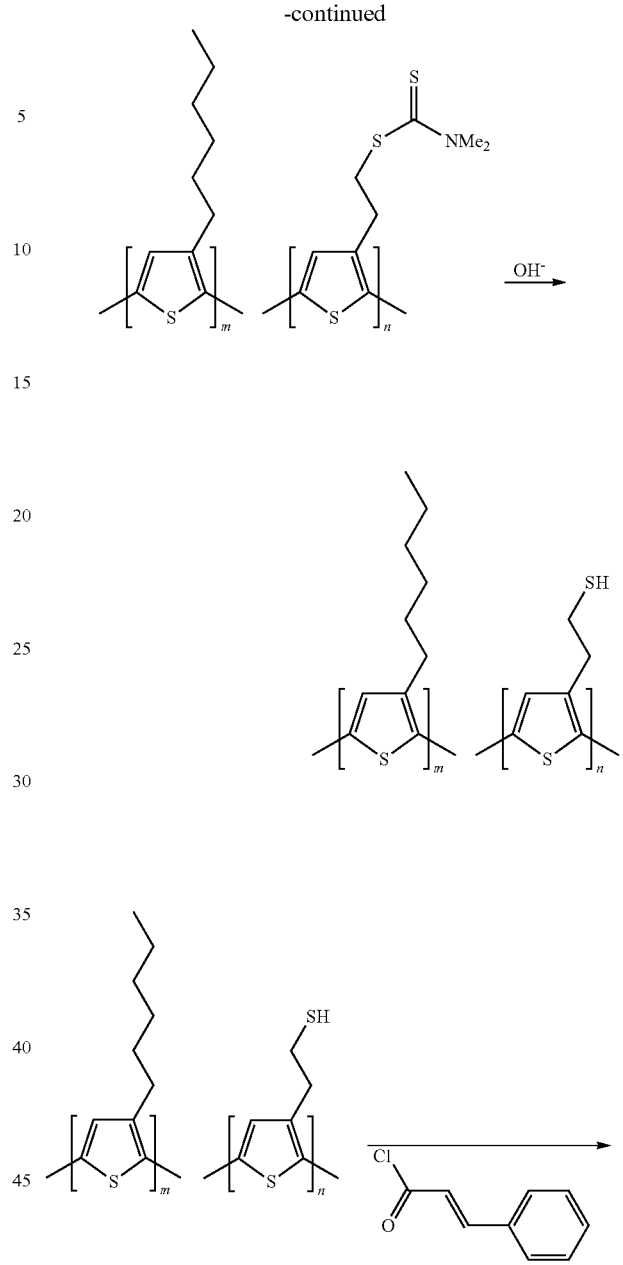
Synthesis of Random Copolymers of
3-hexylthiophene and
3-cinnamoylthioethylthiophene (P15)
The synthesis proceeds according to the following scheme and provides a copolymer comprising recurrent units from a monomer represented by the structural formula (IX) wherein L' is L-SCO-J', L is ethylene and J' is cinnamoyl.
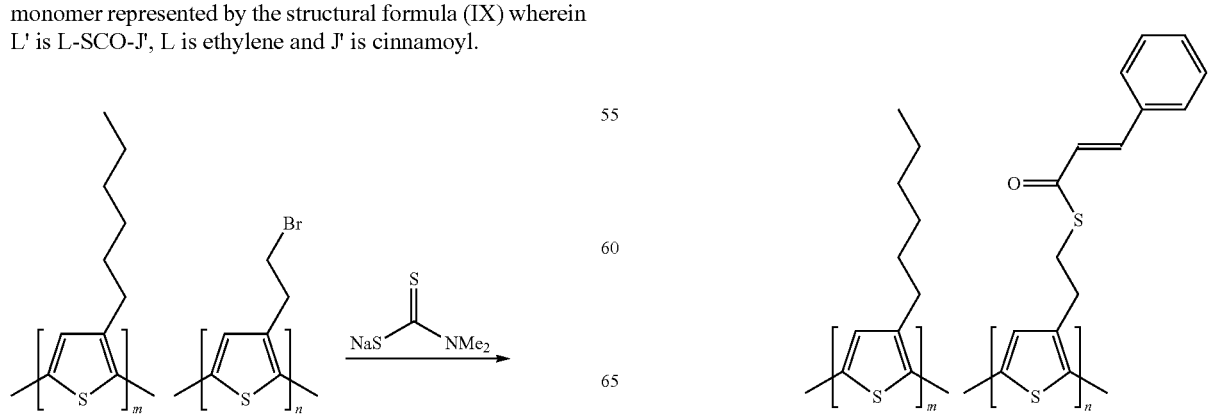

Synthesis of Random Copolymers of 3-hexylthiophene and 3-hexanoic Acid Ethyl Ester P4

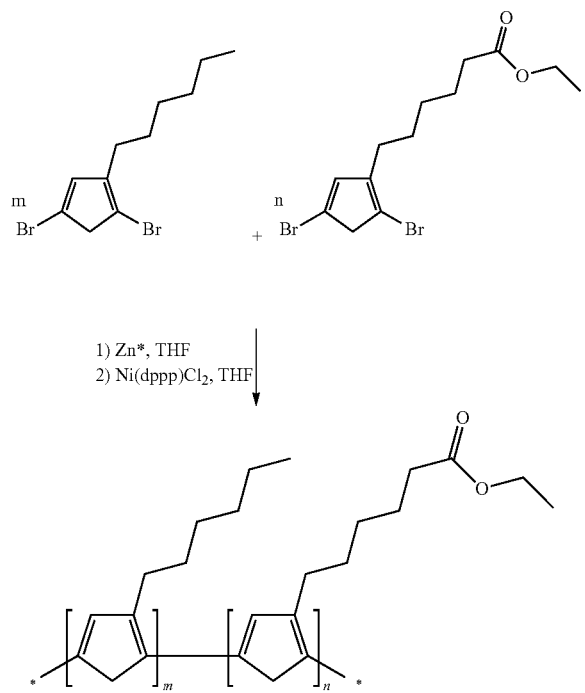

In the scheme above, the stars represent end-groups. Copolymer P4 was synthesized following the Rieke method using active zinc (Zn*) and a nickel catalyst. The monomer solution comprising M1 and M3 monomers in THF was added to Zn* at −78° C. to obtain an organozinc compound. This compound was added to a solution of 0.002 mol % nickel-catalyst in THF and stirred at 60° C. for 18 h under inert atmosphere. The polymers were precipitated in a 2/1 (v/v) mixture of methanol and 2M HCl and purified using a Soxhlet extraction with methanol, pentane and acetone. The polymer was isolated by extraction with chloroform, precipitated in MeOH, filtered and dried. To obtain copolymers with different ratios of hexyl (m) and functionalized (n) side chains, monomer mixtures of various molar compositions were used. The various m/n ratios in the monomer feed before reaction with Zn* allowed to obtain copolymers with different m/n ratios of functional groups.

m/n ratios were chosen to be 9/1, 7/3 and 1/1 to obtain P4 9/1, P4 7/3, and P4 1/1 respectively.

The dibrominated monomers M1 and M3 were mixed in several molar ratios. Respectively 26.8, 28 and 20.1 mmol M1 (8.73, 9.13 and 6.55 g) were mixed with 3, 12 and 20.1 mmol of M3 (1.14, 4.61 and 7.74 g) in a THF solution before applying the polymerization procedure. The P4 copolymer MW increased with an increasing percentage of functionalized side chains: from 56.7 k with D=1.9 for the 9/1 copolymer to 90.5 k, D=2.3 and 199.5 k, D=2.7 for the 7/3 and 1/1 copolymers, respectively. The products of the bulk copolymerization were random copolymers, based on observations in $^1$HNMR.

The M1/M3 ratio in the monomer solution corresponded to the m/n ratio in the copolymers. The solubility of functionalized copolymers P4 was comparable to the solubility of P3HT in organic solvents like chlorobenzene (CB), chloroform (CHCl$_3$) or tetrahydrofurane (THF).

P4 9/1
Yield: 3.77 g, 74%
UV-Vis $\lambda_{max}$ (film)/nm 555, 602sh;
FT-IR (film, ν, cm$^{-1}$):3053, 2953, 2928 and 2854 (C—H), 1738 (C=O), 1563, 1509 and 1455 (C=C), 1376 (CH$_3$), 1260 (w), 1179 and 820 (C—H), 726 (CH$_3$)
$^1$H NMR (300 MHz, CDCl$_3$, δ): 6.96 (1H, s, Th), 4.10 (2H M3, q, OCH$_2$), 2.79 (2H, t, H-T α-CH$_2$), 2.56 (2H, s, H—H α-CH$_2$), 2.31 (2H M3, t, CH$_2$COOEt), 1.69 (2H, br s, β-CH$_2$ and M3), 1.48-1.20 (10H, m, γ, δ, ε-CH$_2$ and γ, δ CH$_2$ M3), 0.90 (6H, t, CH$_3$ M1 and M3).
GPC (THF): Mw=56,700, D=1.9;
Regioregularity: 93%

P4 7/3
Yield: 4.51 g, 61.5%);
UV-vis $\lambda_{max}$ (film)/nm 550, 600sh;
FT-IR (film, ν, cm$^{-1}$): 2926 and 2855 (C—H), 1736 (C=O), 1508 and 1458 (C=C), 1375 (CH$_3$), 1227, 1178 and 824 (C—H), 760 (CH$_3$);
$^1$H NMR (300 MHz, CDCl$_3$, δ): 6.96 (1H, s, Th), 4.10 (2H M3, q, OCH$_2$), 2.79 (2H, br s, H-T α-CH$_2$), 2.56 (2H, s, H—H α-CH$_2$), 2.31 (2H M3, t, CH$_2$COOEt), 1.69 (4H, m, 13-CH$_2$ M1 and M3), 1.54-1.20 (10H, m, γ, δ, ε-CH$_2$ and γ, δ-CH$_2$ M3), 0.89 (6H, t, CH$_3$ M1 and M3).
GPC (THF): Mw=90,500, D=2.3;
Regioregularity: 90%

P4 1/1
Yield: 4.14 g, 53%
$\lambda_{max}$ (film)/nm 550, 604sh;
FT-IR (KBr, ν, cm$^{-1}$):3432 (br, COOH), 2956 (C—H), 1733 (C=O), 1631 and 1454 (C=C), 1259, 1129, 1002 and 867 cm$^{-1}$(C—H),
$^1$H NMR (300 MHz, CDCl$_3$, δ): 6.96 (1H, s, Ar H), 4.10 (2H M3, q, OCH$_2$), 2.79 (2H, t, H-T α-CH$_2$), 2.54 (2H, H—H α-CH$_2$), 2.31 (2H M3, t, CH$_2$COOEt), 1.69 (4H, m, β-CH$_2$ M1 and M3), 1.50-1.20 (10H, m, γ, δ, ε-CH$_2$ M1 and γ, δ-CH$_2$ M3), 0.87 (6H, t, CH$_3$ M1 and M3)
GPC (THF): Mw=119,500, D=2.7;
Regioregularity: 89%

EXAMPLE

Increased Morphological Stability in Side-Chain Functionalized Poly(3 Alkylthiophene):Fullerene Bulk Heterojunction Solar Cells All blends of polymer:PCBM were made in a 1/1 ratio (w/w). PCBM has the following chemical formulae:

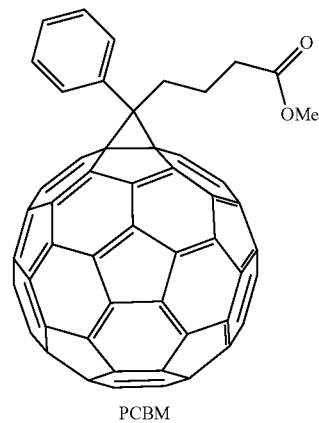

PCBM

Optical micrographs were taken from blends spin-coated on silicon substrates. Solar cells were made on glass ITO patterned substrates. All substrates were cleaned with sonicating in soapy water, Mili-Q water, acetone and heated in isopropanol followed by a UV/O3 treatment. To prepare solar cells, a PEDOT:PSS (Baytron P) layer was spincoated from aqueous solution on the ITO electrode. The polymer:PCBM (1:1) blend was spincoated from a 10 mg mL$^{-1}$ polymer solution in chlorobenzene and annealed for 15 minutes at 100° C. on a hotplate. As a cathode, typically 20 nm Ca and 80 nm Al were deposited in high vacuum (p=1.10$_{-6}$ mbar). I-V measurements were performed in $N_2$ atmosphere under AM 1.5G simulation, using an Oriel simulator equipped with a 150 W Xenon short arc lamp while the samples were kept under continuous annealing.

Accelerated lifetime testing was done in a heating chamber which was developed for this purpose. The solar cells were kept in the dark, lighting only for I-V characterization every 30 minutes, while the experiment's temperature was kept constant. Solar cell characteristics in FIGS. 11-19 are given relative to their initial value at time to at the experiments' temperature. Solar cell characteristics in FIGS. 20-27 are not given relative to their initial value. They are absolute. XRD measurements were done on a Siemens D5000 diffractometer in θ-2θ mode.

The incident beam used is the CuKα1 line of a Ge(111) monochromator, with a λ=0.154056 nm. Differential scanning calorimetry (DSC) was done to measure the melting temperature ($T_m$) and melting enthalpy ($H_m$) on a TA Instruments Q2000 (Tzero™) with Refrigerator Cooling System (RCS) and nitrogen 50 mL min$_{-1}$, aluminum Tzero™ crucible at a scan rate of 10.0 K min$^{-1}$. The first cooling and second heating run were used for discussion.

The performance of these copolymers in BHJ solar cells depended on the percentage of the functionalized side chains in the copolymer. The short circuit current ($J_{sc}$) and PCE decrease with a higher percentage of functionalized side chains.

Figure 2:
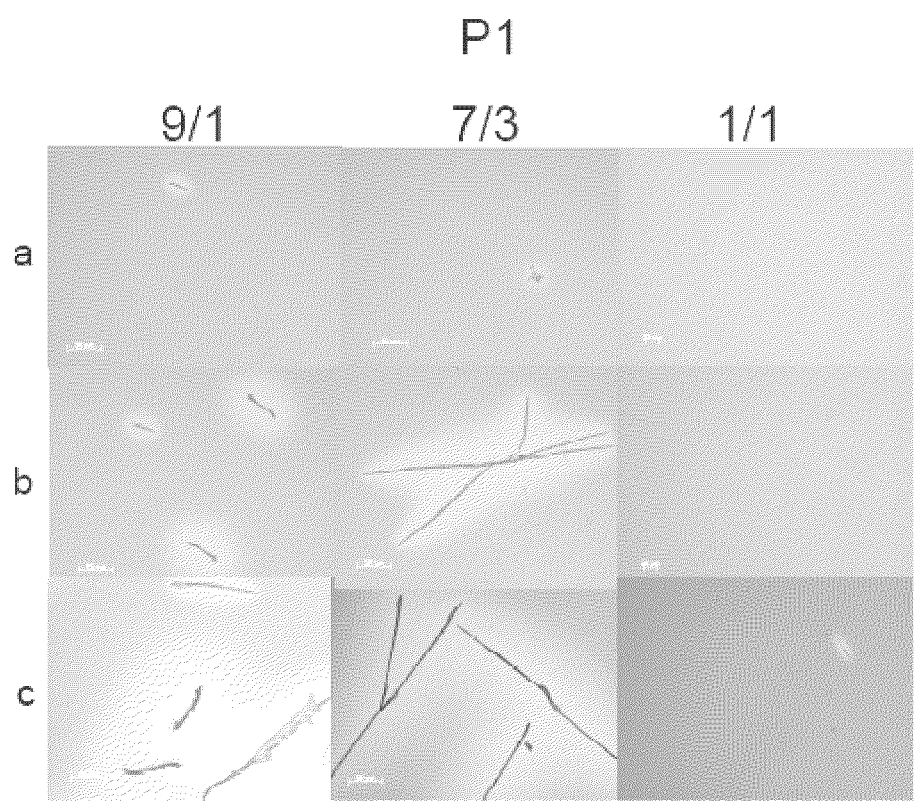
FIG. 2 shows optical micrographs of a P1 9/1:PCBM 1:1 blend (left, embodiment), a P1 7/3:PCBM 1:1 blend (middle, embodiment) and a P1 1/1:PCBM blend (right, embodiment) annealed at 125° C. for a) 15 min, b) 2 h, and c) 24 h.
Figure 3:
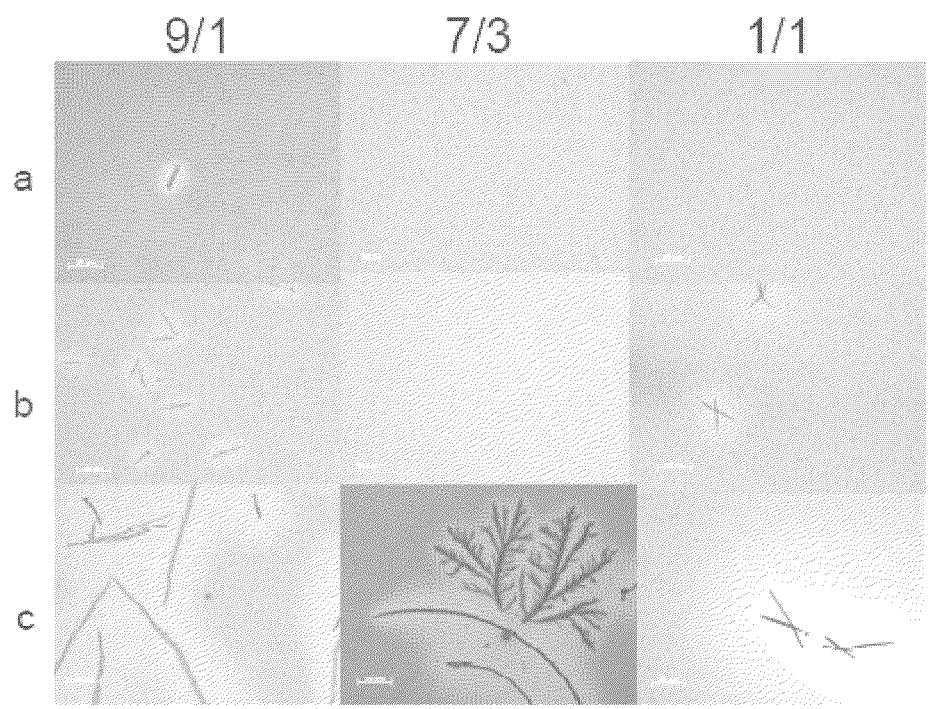
FIG. 3 shows optical micrographs of a P3 9/1:PCBM 1:1 blend (left, embodiment), a P3 7/3:PCBM 1:1 blend (middle, embodiment), and a P3 1/1:PCBM blend (right, embodiment) annealed at 125° C. for a) 15 min, b) 2 h, and c) 24 h.
Figure 4:
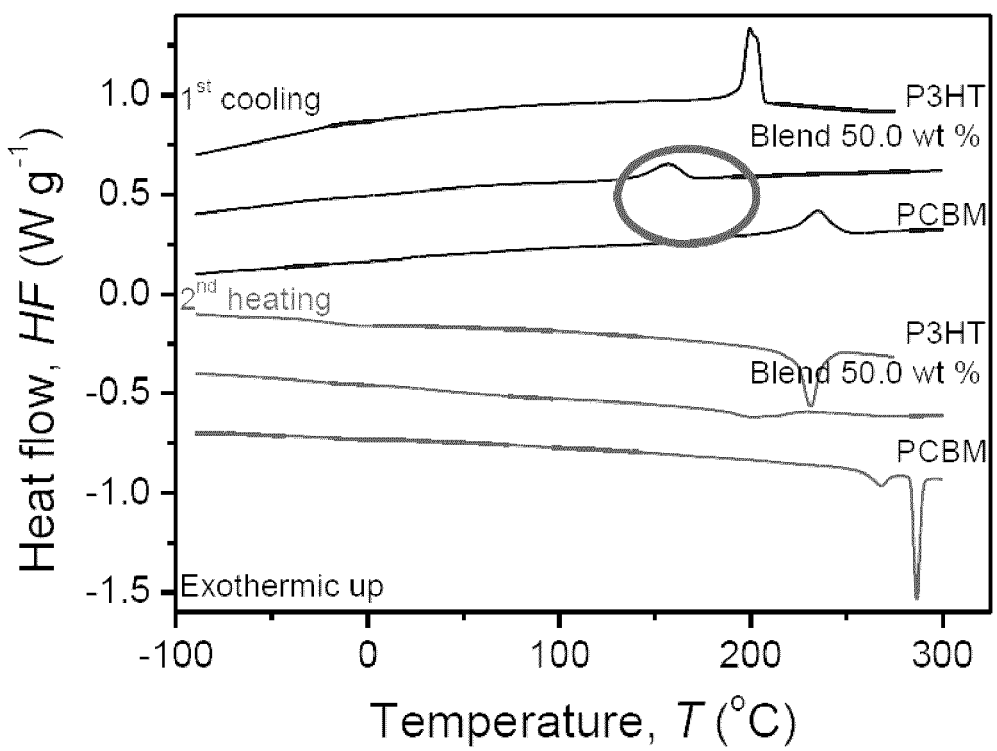
FIG. 4 shows a DSC curve of P3HT(comparative), its 1:1 blend with PCBM (comparative) and PCBM alone (comparative); "HF" stands for heat flow and "T" for temperature.
Figure 5:
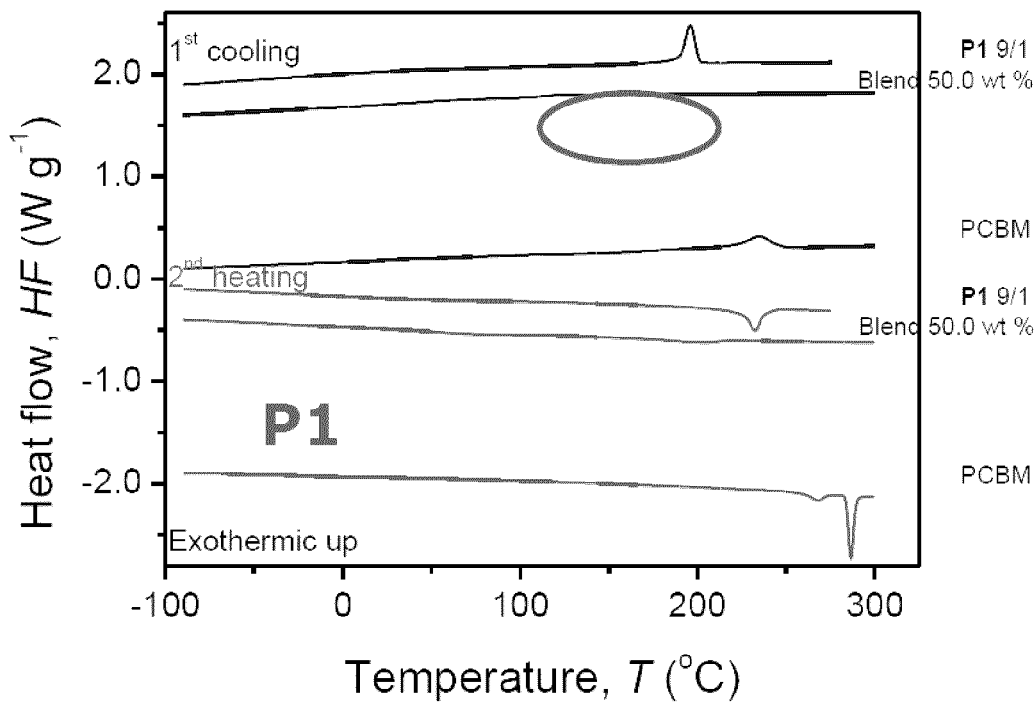
FIG. 5 shows a DSC curve of P1 9/1 (embodiment), its 1:1 blend with PCBM (embodiment) and PCBM alone (comparative); "HF" stands for heat flow and "T" for temperature.
Figure 6:
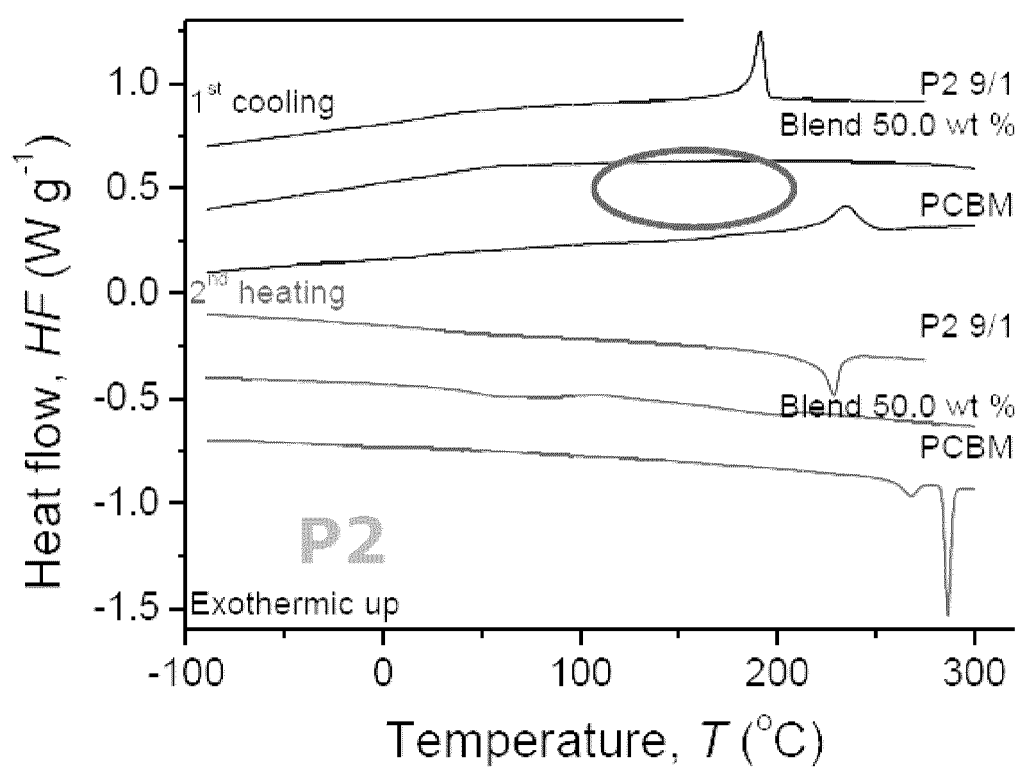
FIG. 6 shows a DSC curve of P2 9/1 (embodiment), its 1:1 blend with PCBM (embodiment) and PCBM alone (comparative); "HF" stands for heat flow and "T" for temperature.
Figure 7:
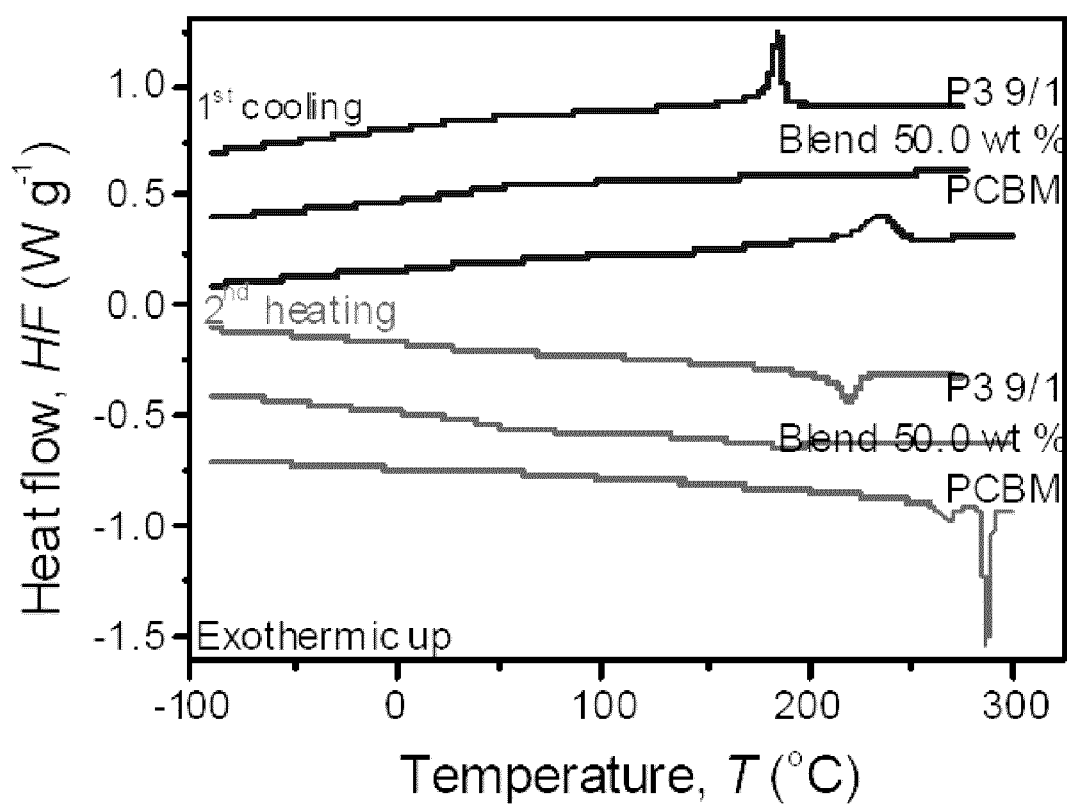
FIG. 7 shows a DSC curve of P3 9/1 (embodiment), its 1:1 blend with PCBM (embodiment) and PCBM alone (comparative); "HF" stands for heat flow and "T" for temperature.

In optical microscopy pictures of polymer:PCBM (1:1, w/w) blends (FIG. 1), it is observed that after 15 minutes at 125° C. there are plenty of μm-scale PCBM crystals visible for the P3HT:PCBM blend. These needle-like crystals are created when PCBM diffuses out of the blend and crystallizes. In blends of the copolymers according to embodiments of the present invention with PCBM however, the needle formation is suppressed. After 15 minutes at 125° C. for P2 9/1 there are no needles visible at all, for P3 9/1 occasionally a PCBM needle can be found. With longer annealing times, the number of PCBM crystals increases strongly in the P3HT:PCBM blend but only slightly in the copolymer:PCBM blends according to embodiments of the present invention, indicating a thermally more stable morphology in the copolymer blends. With an increasing degree of functionalization, less PCBM crystals were observed (see FIG. 2 for the case of the P1:PCBM blends and FIG. 3 for the case of the P3:PCBM blends).

Figure 8:
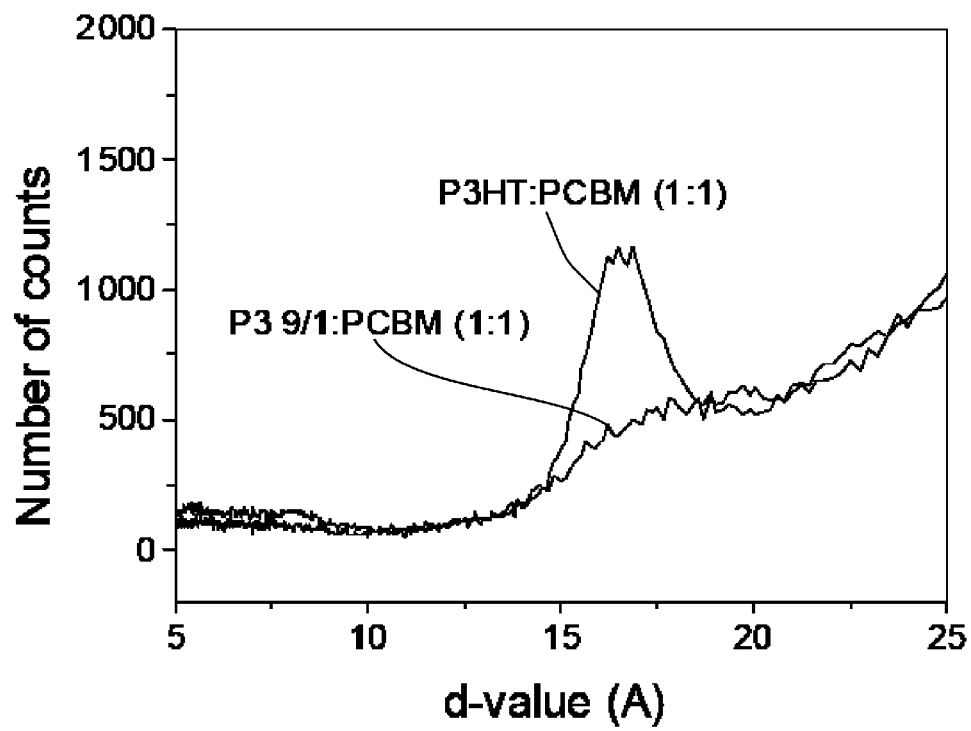
FIG. 8 shows XRD diffraction patterns of P3HT:PCBM 1:1 (comparative) and P3 9/1:PCBM 1:1 (embodiment) before annealing; "N" stands for the number of counts and "d" stands for d-value.
Figure 9:
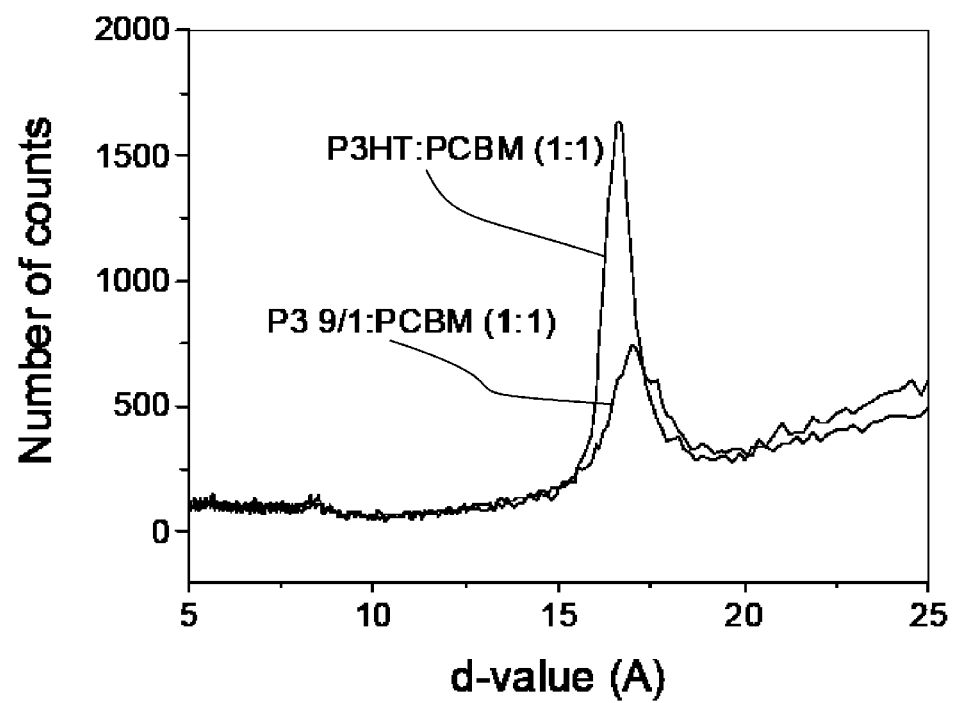
FIG. 9 shows XRD diffraction patterns of P3HT:PCBM 1:1 after 15 min at 125° C. (comparative) and P3 9/1:PCBM 1:1 after 15 min at 125° C. (embodiment); "N" stands for the number of counts and "d" stands for d-value.
Figure 10:
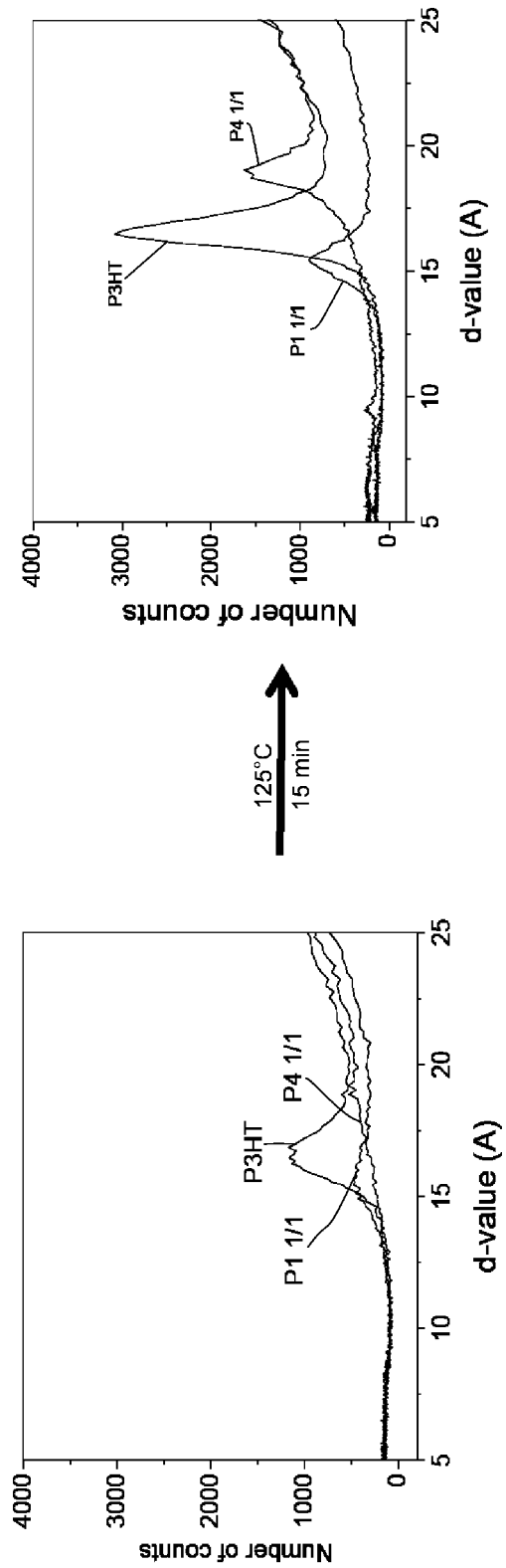
FIG. 10 shows XRD diffraction patterns of P3HT:PCBM 1:1 (comparative), P1 1/1:PCBM 1:1 (embodiment) and P4 1/1:PCBM 1:1 (embodiment) before annealing and after 15 min at 125° C.; "N" stands for the number of counts and "d" stands for d-value.

X Ray Diffractions (XRD) were performed on copolymer:PCBM blends to collect more information on the crystallization phenomena (see FIG. 8-10). In P3HT:PCBM blends spin-coated from chlorobenzene, the lamellar stacking in P3HT had a d-spacing around 17.0 Å (see FIG. 8 and FIG. 10 left side). Upon annealing (FIG. 9 and FIG. 10 right side), the diffraction peak narrowed, presumably caused by a directional alignment of polymer chains. In P3 9/1:PCBM blends, no crystalline signal is visible in films spincoated from PCBM (FIG. 8). Upon annealing 15 minutes at 125° C., the crystalline diffraction signal was detected but this was broader compared to P3HT, indicating that the orientation of the formed crystallites is less defined (FIG. 9). Similar observations were made for P1 1/1 and P4 1/1 (see FIG. 10). The heating and cooling DSC curves for P3HT, the P1 9/1, P2 9/1 and P3 9/1 copolymers and their (1/1) blends with PCBM are displayed in FIGS. 4, 5, 6 and 7, respectively. For P3HT:PCBM blends there is a single crystallization peak visible in the first cooling curve. At the same scan rate of 10 K min$^{-1}$ however, no crystallization can be measured for the copolymer:PCBM blends. Although the crystallization of PCBM is visible in optical microscopy and the crystalline stacking in the copolymer was clear in XRD, the presence of functionalized side chains affected the crystallization kinetics of the two materials in the blend in such a way that no melting or crystallization could be detected with DSC.

To verify if the increased thermal morphological stability in the blend was also reflected on the thermal stability of the BHJ solar cell, several ITO/PEDOT:PSS/polymer:PCBM(1:1)/Ca/Al devices were subjected to higher temperatures for a specific time. The efficiencies, relative to the first measurement at the experiment's temperature, are displayed in FIG. 11-19.

Figure 11:
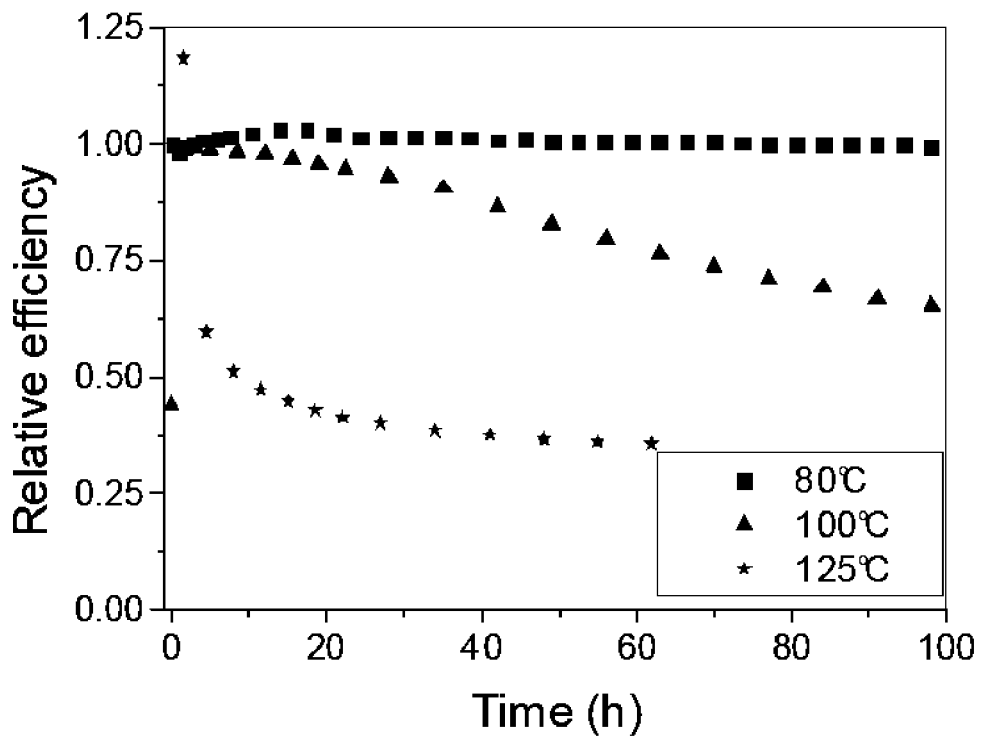
FIG. 11 shows the relative efficiency as a function of time for ITO/PEDOT/P3HT:PCBM 1:1/Ca/Al solar cells (comparative) at 80° C. (squares), 100° C. (triangles) and 125° C. (stars).

The relative efficiency of P3HT:PCBM solar cells are displayed in FIG. 11 as a function of time for several temperatures. At 80° C., the device efficiency is fairly constant for at least 100 h. At 100° C. and 125° C., the efficiency of the P3HT:PCBM device decreases increasingly fast. When looking at the device parameters on FIG. 14-19, the degradation of $J_{sc}$ is largely responsible for the decreasing efficiency. As the phase separation continues in the blend morphology, and proceeds increasingly fast with higher temperatures within a certain range, less excitons are dissociated and less current is generated, therefore $J_{sc}$ is the most appropriate parameter to correlate with morphological stability. The decrease in FF (see FIG. 16) and $V_{oc}$ (see FIG. 15) may also be related to reorganization effects in the blend, but other ageing mechanisms cannot be excluded at these temperatures and in this time interval.

Figure 12:
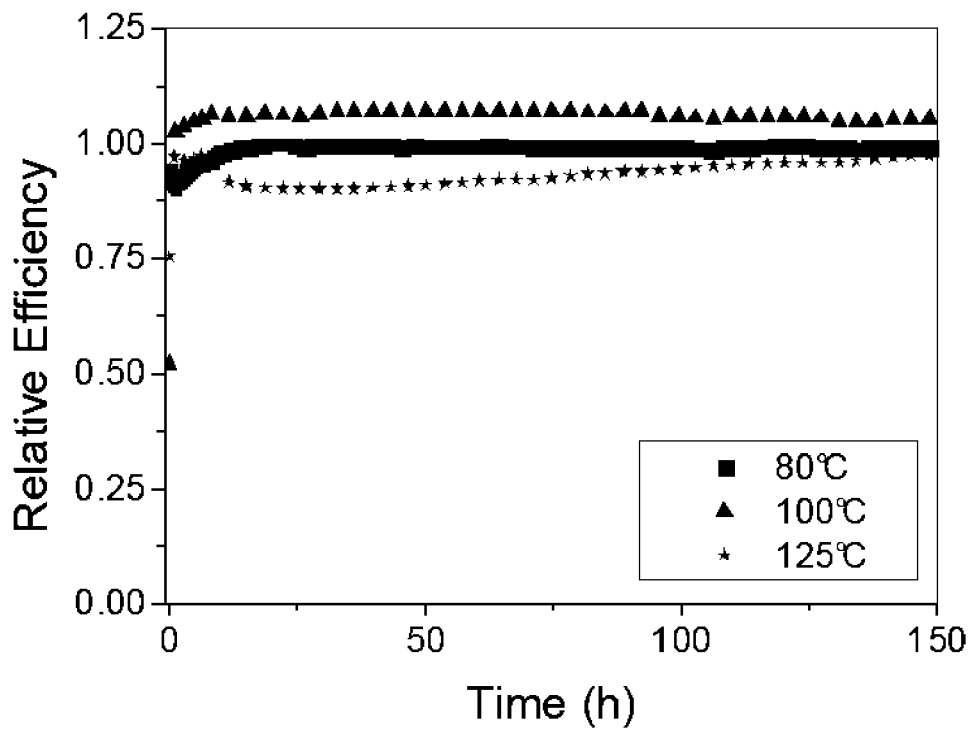
FIG. 12 shows the relative efficiency as a function of time for ITO/PEDOT/P3 9/1:PCBM 1:1/Ca/Al solar cells (embodiment) at 80° C. (squares), 100° C. (triangles) and 125° C. (stars)
Figure 13:
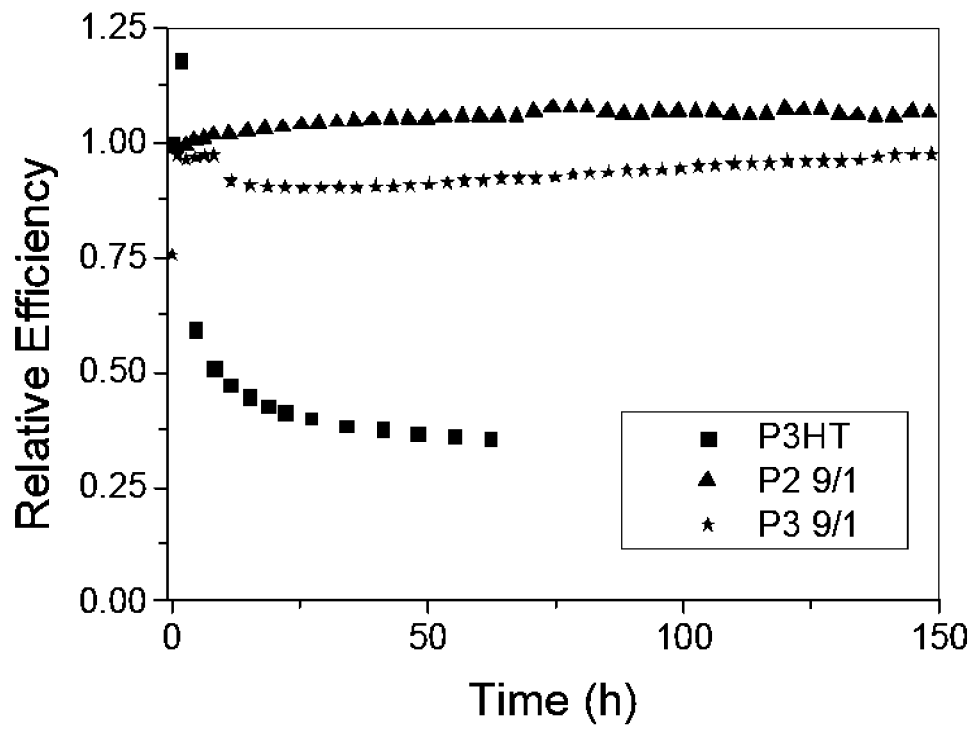
FIG. 13 shows the relative efficiency as a function of time for ITO/PEDOT/polymer:PCBM 1:1/Ca/Al solar cells wherein the polymer is either P3HT (squares, comparative), P2 9/1 (triangles, embodiment) or P3 9/1 (stars, embodiment) at 125° C.
Figure 14:
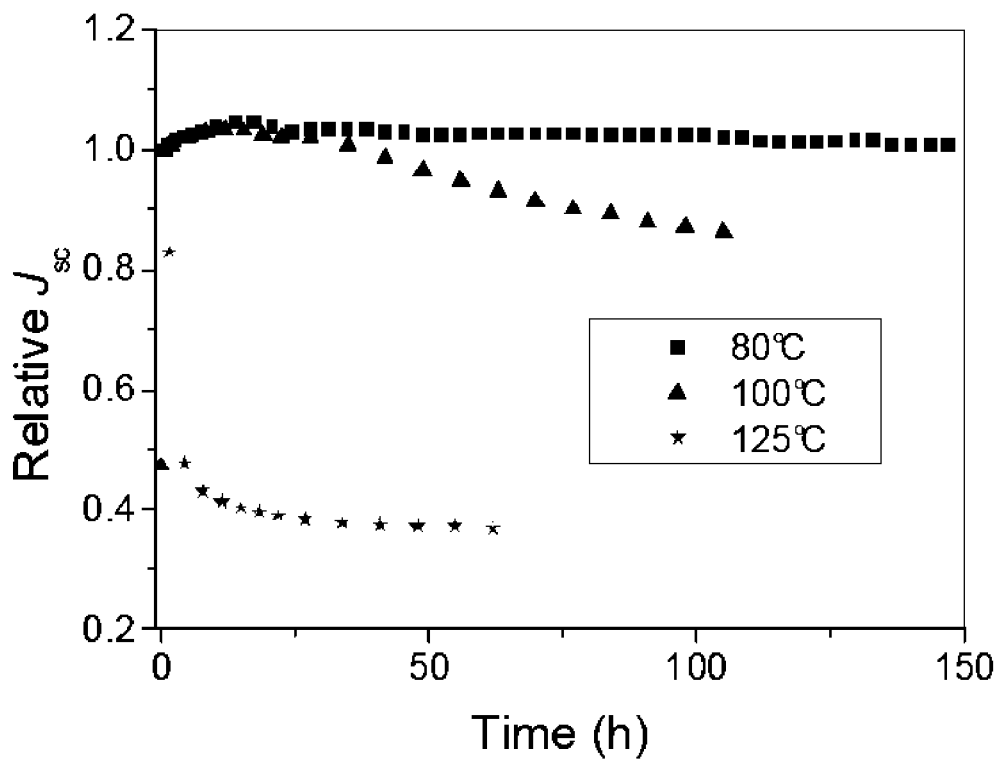
FIG. 14 shows the relative current density as a function of time for ITO/PEDOT/P3HT:PCBM 1:1/Ca/Al solar cells at 80 (squares), 100 (triangles) and 125° C. (stars) (comparative).
Figure 15:
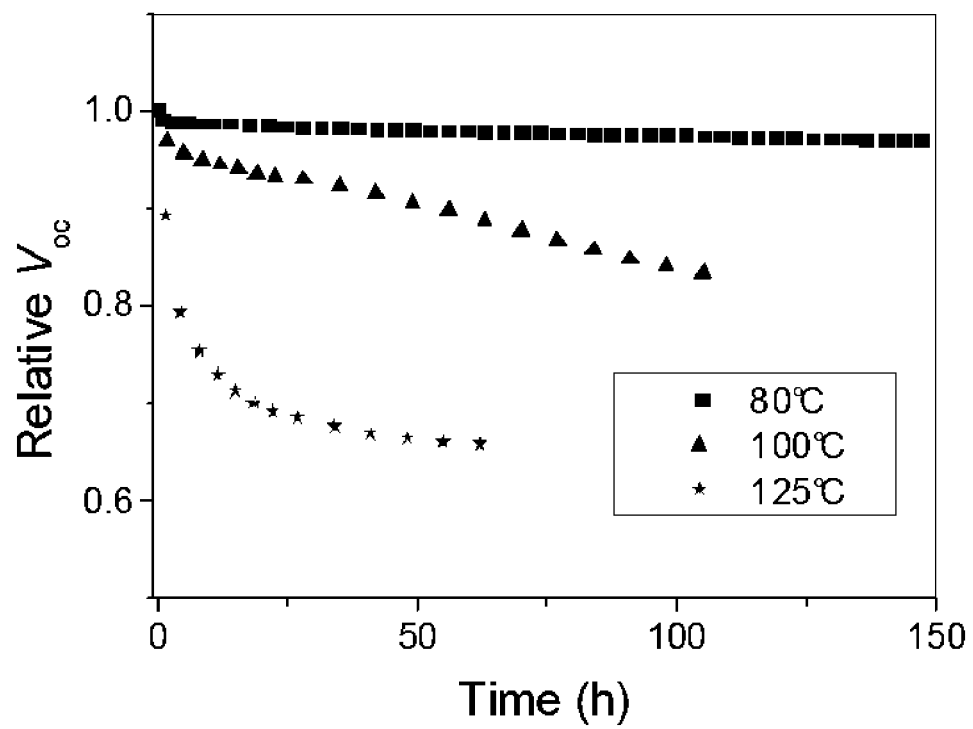
FIG. 15 shows the relative open circuit voltage as a function of time for ITO/PEDOT/P3HT:PCBM 1:1/Ca/Al solar cells at 80 (squares), 100 (triangles) and 125° C. (stars) (comparative).
Figure 16:
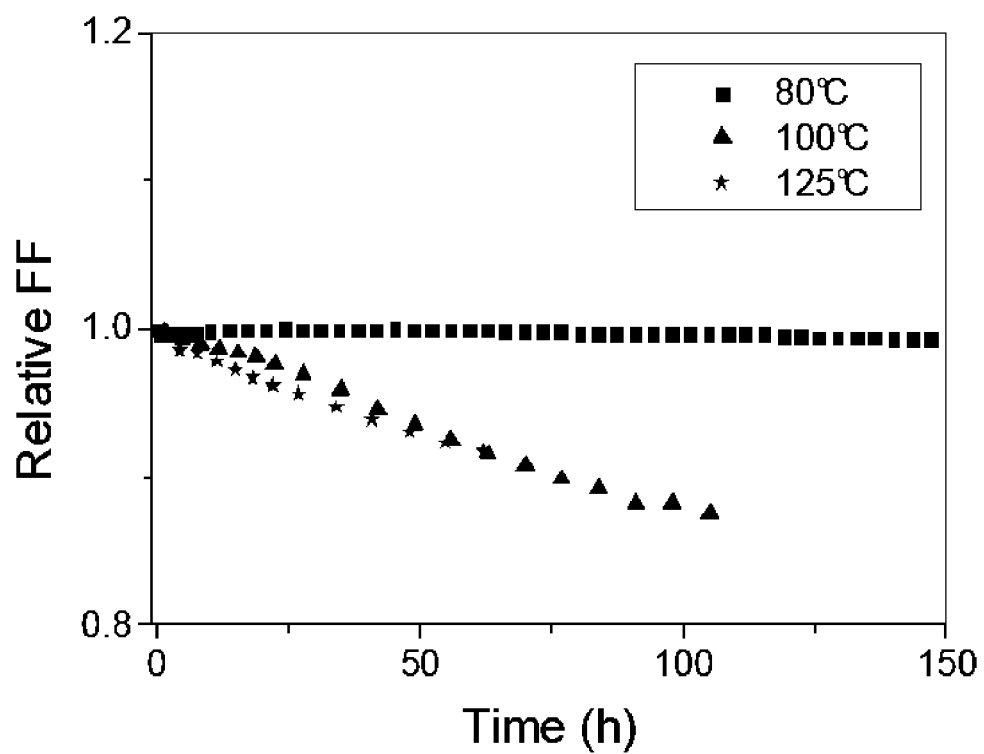
FIG. 16 shows the relative fill factor as a function of time for ITO/PEDOT/P3HT:PCBM 1:1/Ca/Al solar cells at 80 (squares), 100 (triangles) and 125° C. (stars) (comparative).
Figure 17:
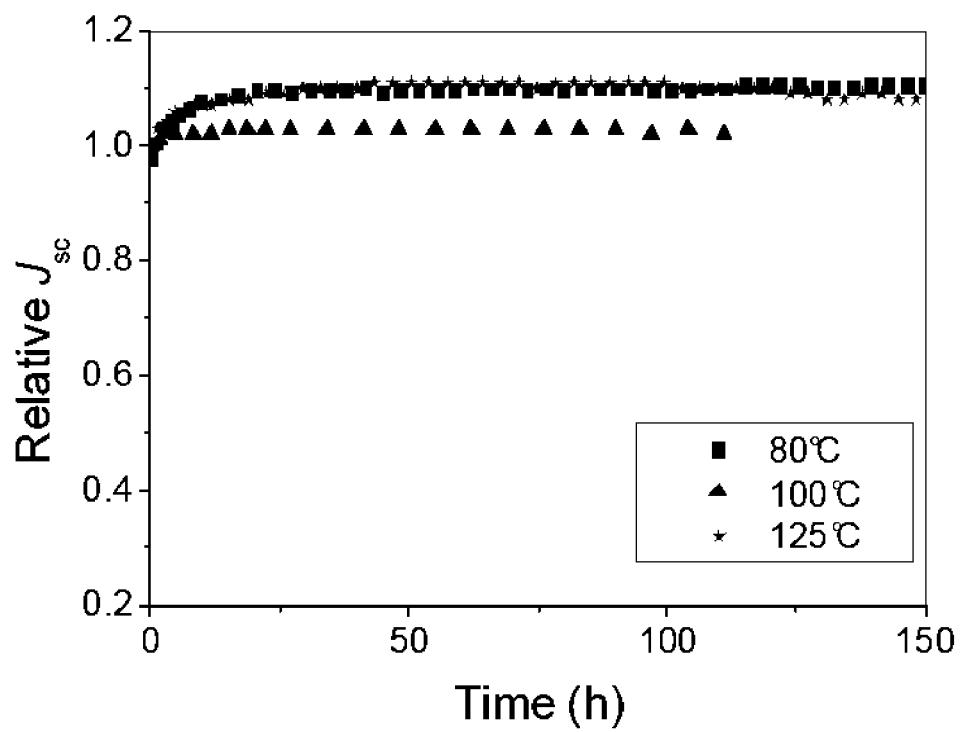
FIG. 17 shows the relative current density as a function of time for ITO/PEDOT/P3 9/1:PCBM 1:1/Ca/Al solar cells at 80 (squares), 100 (triangles) and 125° C. (stars) (embodiment).
Figure 18:
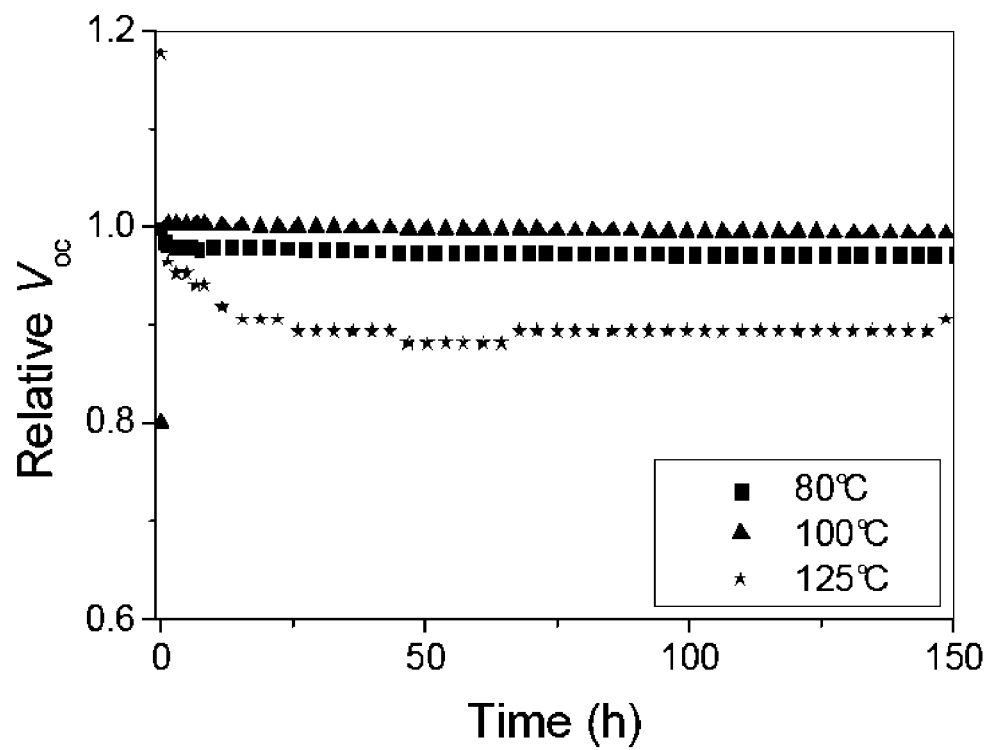
FIG. 18 shows the relative open circuit voltage as a function of time for ITO/PEDOT/P3 9/1:PCBM 1:1/Ca/Al solar cells at 80 (squares), 100 (triangles) and 125° C. (stars) (embodiment).
Figure 19:
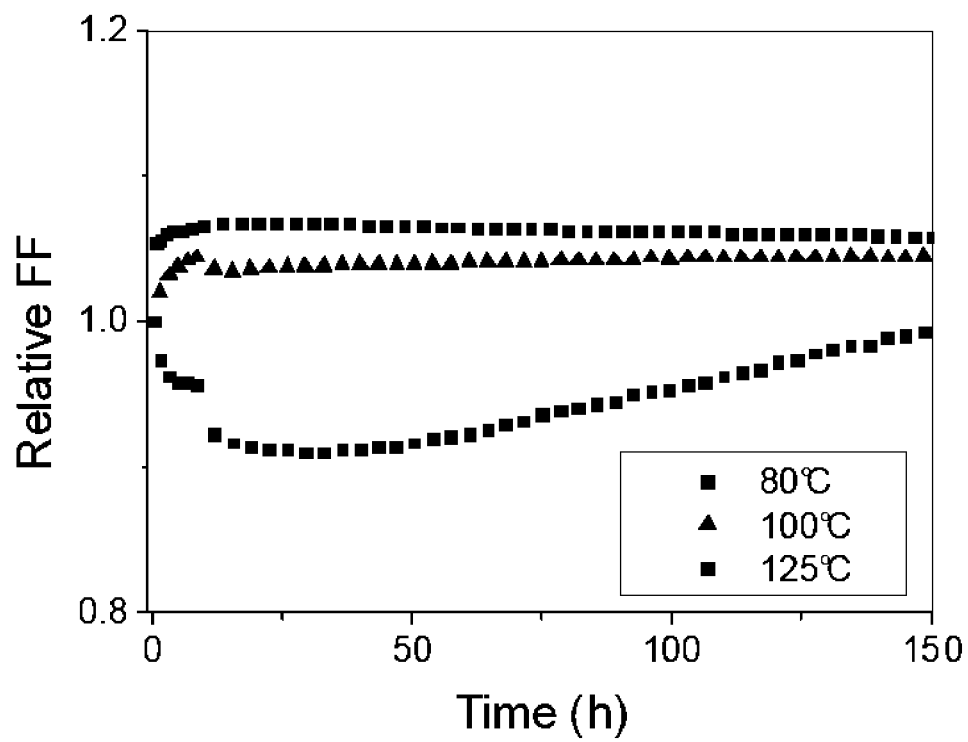
FIG. 19 shows the relative fill factor as a function of time for ITO/PEDOT/P3 9/1:PCBM 1:1/Ca/Al solar cells at 80 (squares), 100 (triangles) and 125° C. (stars) (embodiment).
Figure 20:
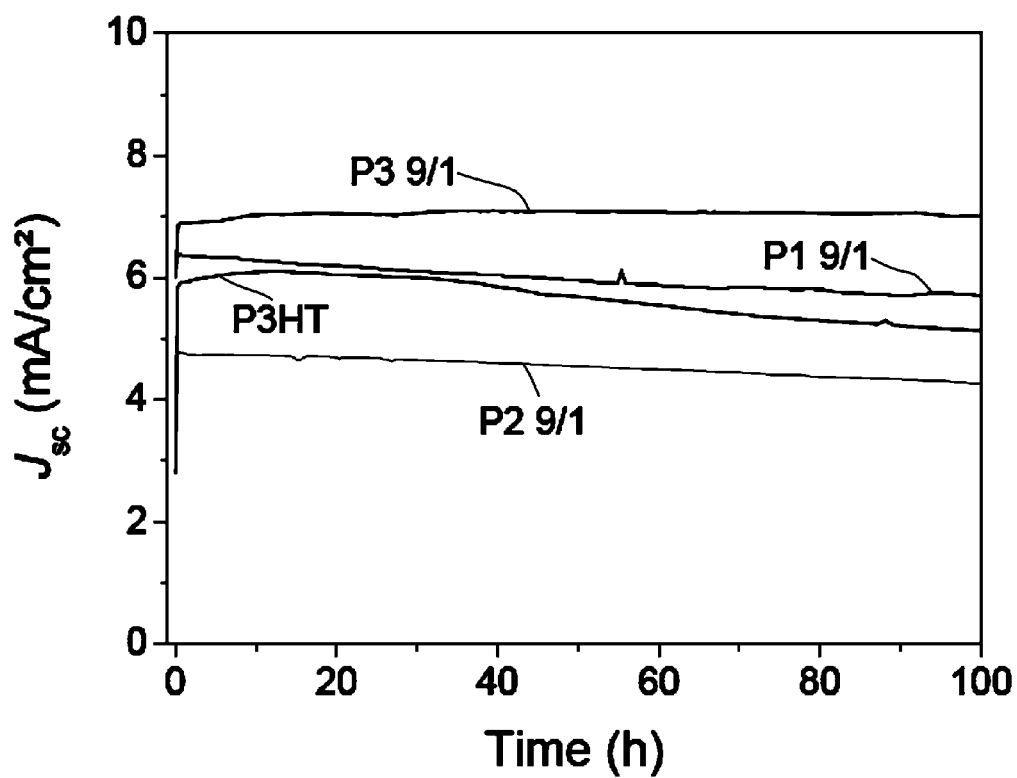
FIG. 20 shows the short circuit current density as a function of time for ITO/PEDOT/polymer:PCBM 1:1/Ca/Al solar cells at 100° C. wherein the polymer is either P3HT (comparative), P1 9/1 (embodiment), P2 9/1 (embodiment), or P3 9/1 (embodiment).
Figure 21:
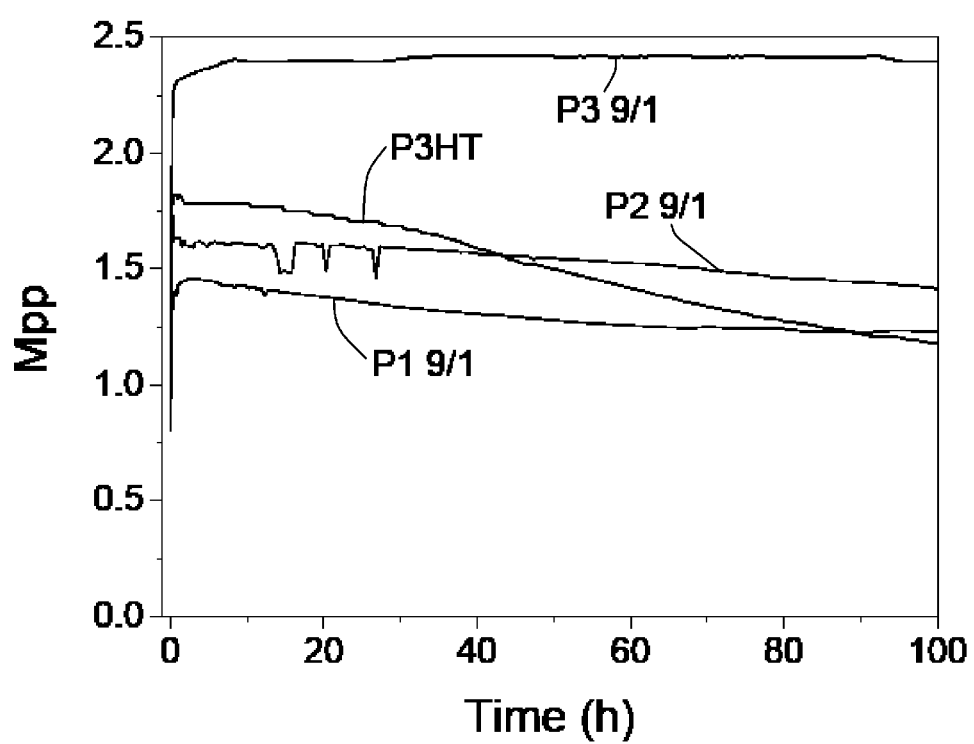
FIG. 21 shows the maximum power point as a function of time for ITO/PEDOT/polymer:PCBM 1:1/Ca/Al solar cells at 100° C. wherein the polymer is either P3HT (comparative), P1 9/1 (embodiment), P2 9/1 (embodiment), or P3 9/1 (embodiment).
Figure 22:
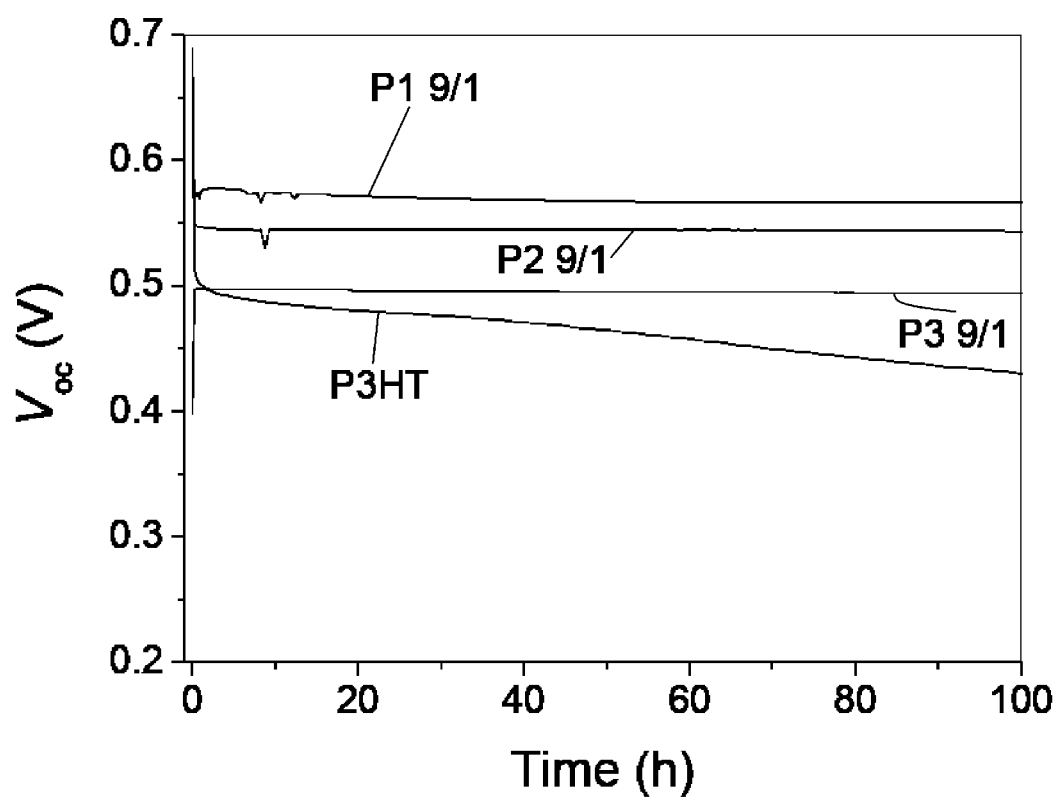
FIG. 22 shows the open circuit voltage as a function of time for ITO/PEDOT/polymer:PCBM 1:1/Ca/Al solar cells at 100° C. wherein the polymer is either P3HT (comparative), P1 9/1 (embodiment), P2 9/1 (embodiment), or P3 9/1 (embodiment).
Figure 23:
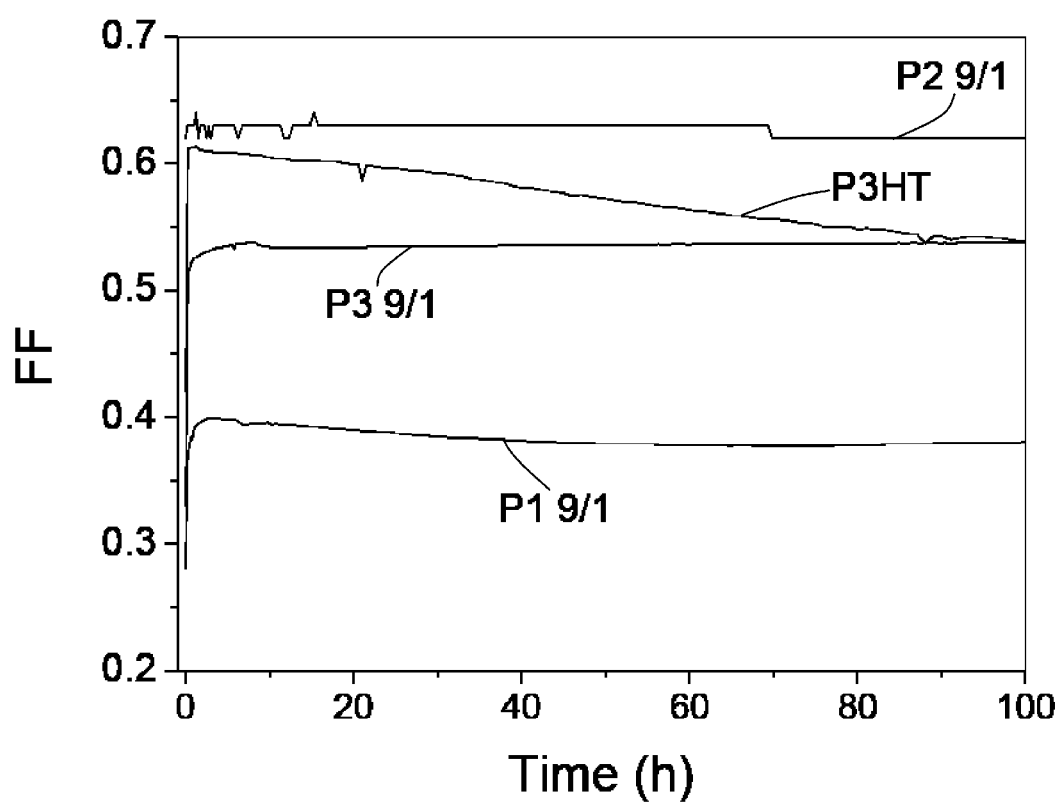
FIG. 23 shows the fill factor as a function of time for ITO/PEDOT/polymer:PCBM 1:1/Ca/Al solar cells at 100° C. wherein the polymer is either P3HT (comparative), P1 9/1 (embodiment), P2 9/1 (embodiment), or P3 9/1 (embodiment).
Figure 24:
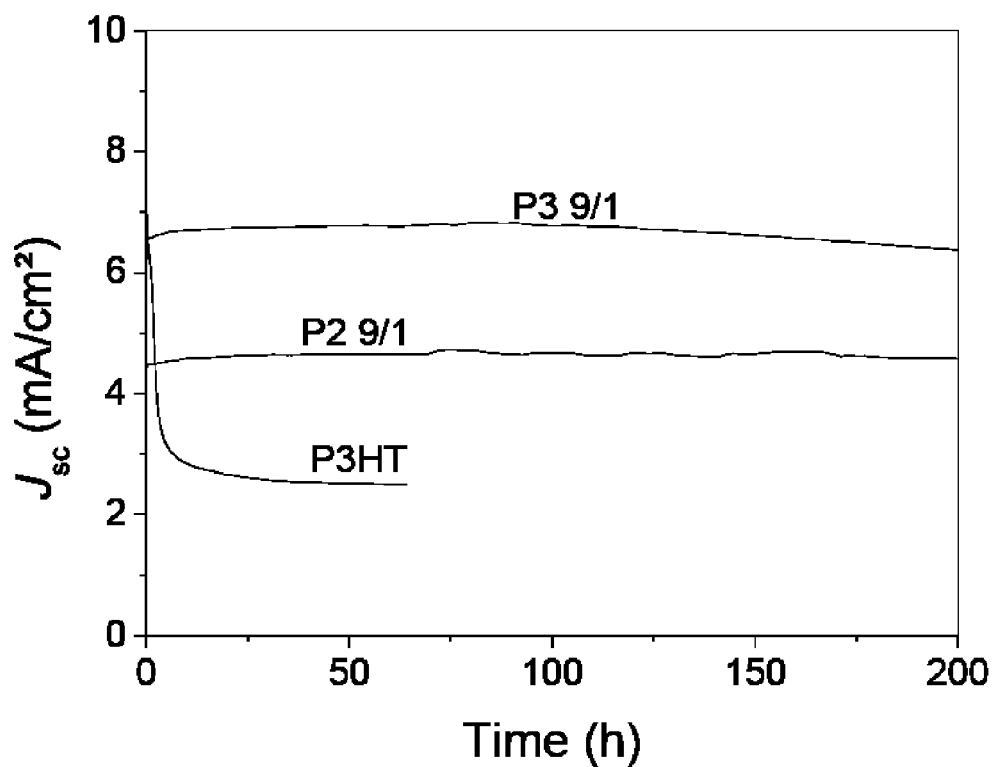
FIG. 24 shows the short circuit current density as a function of time for ITO/PEDOT/polymer:PCBM 1:1/Ca/Al solar cells at 125° C. wherein the polymer is either P3HT (comparative), P2 9/1 (embodiment), or P3 9/1 (embodiment).
Figure 25:
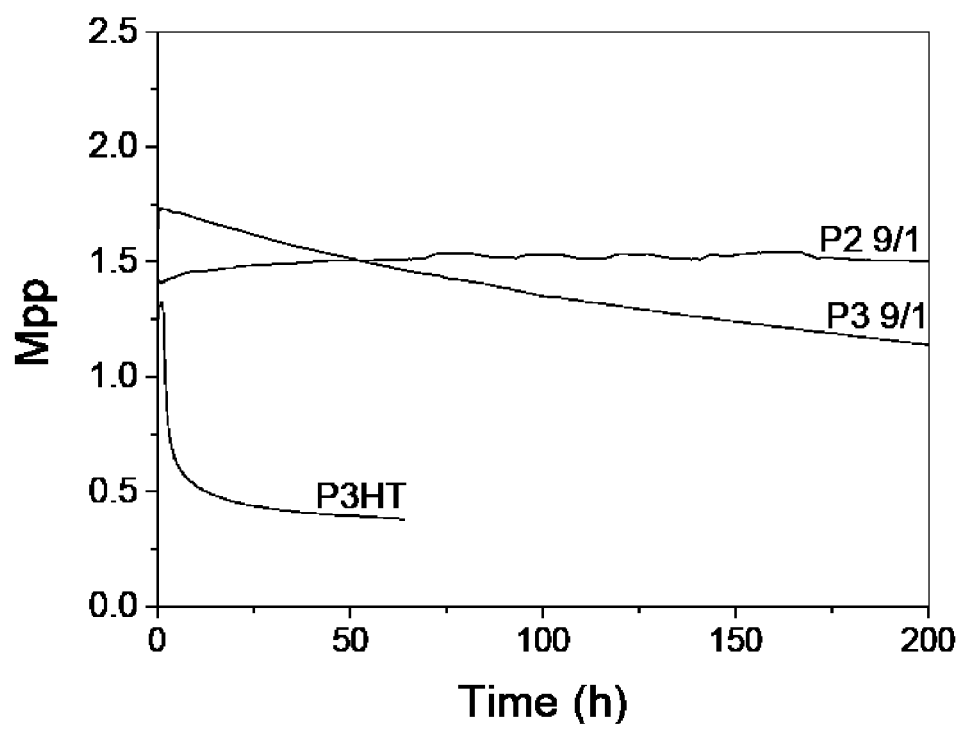
FIG. 25 shows the maximum power point as a function of time for ITO/PEDOT/polymer:PCBM 1:1/Ca/Al solar cells at 125° C. wherein the polymer is either P3HT (comparative), P2 9/1 (embodiment), or P3 9/1 (embodiment).
Figure 26:
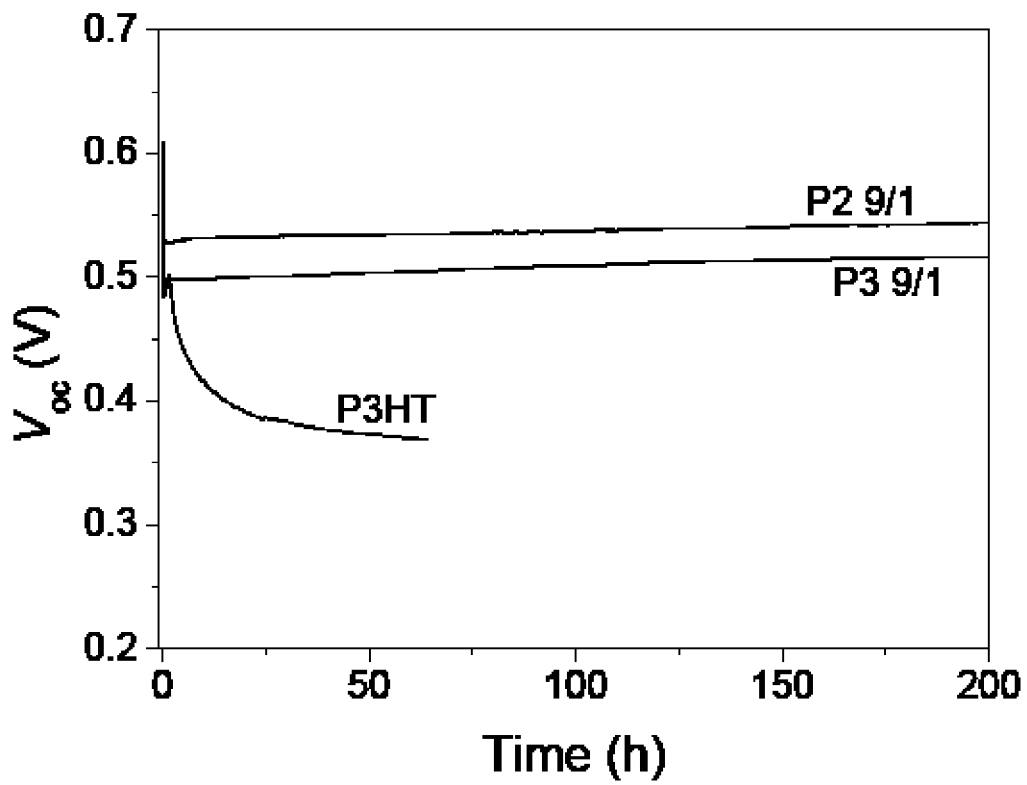
FIG. 26 shows the open circuit voltage as a function of time for ITO/PEDOT/polymer:PCBM 1:1/Ca/Al solar cells at 125° C. wherein the polymer is either P3HT (comparative), P2 9/1 (embodiment), or P3 9/1 (embodiment).
Figure 27:
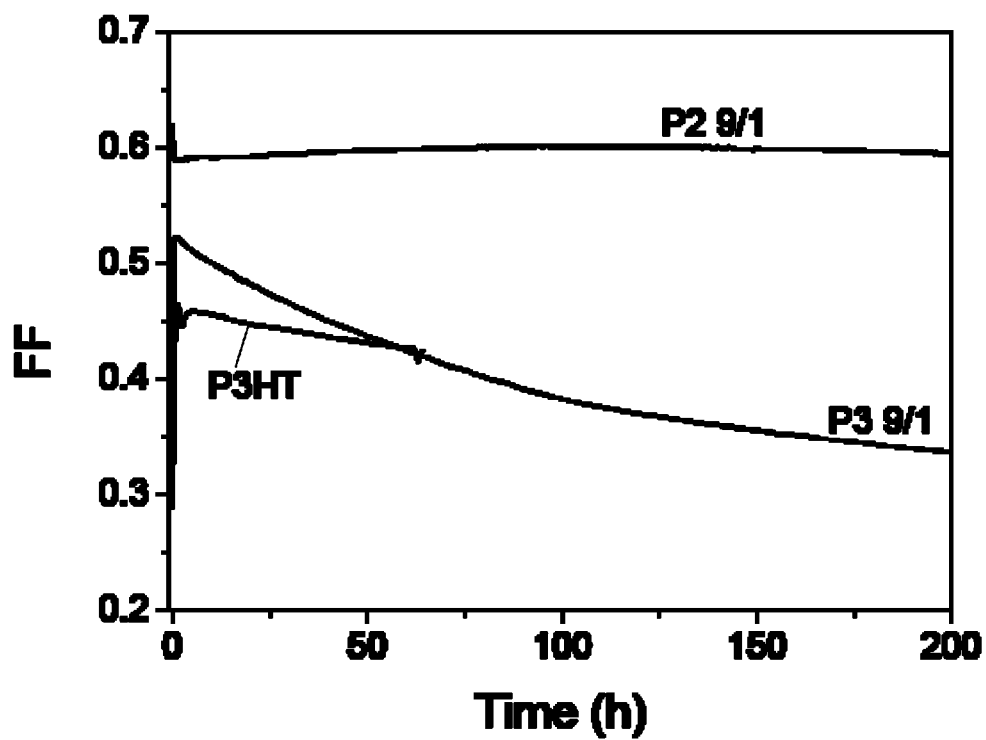
FIG. 27 shows the fill factor as a function of time for ITO/PEDOT/polymer:PCBM 1:1/Ca/Al solar cells at 125° C. wherein the polymer is either P3HT (comparative), P2 9/1 (embodiment), or P3 9/1 (embodiment).

In FIG. 12, the evolution of P3 9/1 copolymer solar cells efficiency is given at several temperatures. Here, the efficiency is less dependent on temperature, and is quite stable even at 125° C. for 150 h. From the device parameters FIG. 17-19, the constant $J_{sc}$ (FIG. 17) points to a thermally more stable morphology in the P3 9/1:PCBM solar cells: after 150 h no degradation of the photocurrent could be observed. The FF and $V_{oc}$ showed fluctuations of about 10% relative to the initial value throughout the testing period. In FIG. 13, the device efficiency of P3HT solar cells at 125° C. is compared to that of devices made with P2 9/1 and P3 9/1 copolymer blends.

FIG. 20-23 show the absolute short circuit current density, the absolute maximum power point, the absolute open circuit voltage and the absolute fill factor for P3HT, P1 9/1, P2 9/1 and P3 9/1 solar cells in function of time upon continuous annealing at 100° C. There also, the solar cell performance is clearly much more stable in the case of the blends according to the present invention that in the P3HT:PCBM blend.

FIG. 24-27 show the absolute short circuit current density, the absolute maximum power point, the absolute open circuit voltage and the absolute fill factor for P3HT, P2 9/1 and P3 9/1 solar cells in function of time upon continuous annealing at 100° C. There also, the solar cell performance is clearly much more stable in the case of the blends according to the present invention that in the P3HT:PCBM blend.

The $J_{sc}$ and efficiency of the P3HT solar cells decreases much more rapidly compared to the copolymer solar cells. The morphology in a copolymer:PCBM blend according to embodiments of the present invention is much less sensitive to reorganization compared to P3HT, resulting in the increased thermal stability of copolymer:PCBM solar cells. Introducing 10% of functionalized side chains does not affect the power conversion efficiency (PCE) significantly when compared to P3HT:PCBM devices processed according to the same procedure, but increases the morphological stability.

Although there is some crystallization in a copolymer: PCBM blends (PCBM crystallization visible with optical microscopy, crystalline P3HT stacking in XRD), the presence of the functionalized side chains slows down the crystallization rate (not visible with DSC at 10 K min$^{-1}$) which stabilizes the blend morphology. The stable blend morphology in the device leads to a more stable photocurrent in solar cells at 125° C. The increased thermal morphological stability for the 9/1 copolymers presents a compromise between high efficiency and increased thermal stability in polythiophene: fullerene bulk heterojunction solar cells.

What is claimed is:

1. A blend for use in a photovoltaic device, comprising:
   (a) a polymer, wherein the polymer is selected from the group consisting of a random co-polymer, an alternating co-polymer, and a block co-polymer, and wherein the polymer comprises at least one comonomer of formula (VII):

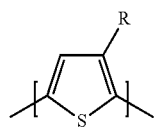

(VII)

wherein R is selected from the group consisting of a linear alkyl group having from 6 to 10 carbon atoms and a branched alkyl group having from 6 to 10 carbon atoms; and monomer units of formula (IV):

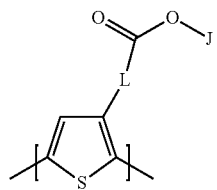

(IV)

wherein L is selected from the group consisting of a linear alkylene group having 5 carbon atoms and a branched alkylene group having 5 carbon atoms; and J is selected from the group consisting of a hydrogen atom, a linear alkyl group having from 1 to 4 carbon atoms, and a branched alkyl group having from 1 to 4 carbon atoms; and (b) an electron acceptor, wherein the electron acceptor is a fullerene derivative, wherein the fullerene derivative is [6,6]-phenyl-$C_{61}$-butyric acid methyl ester, the blend having 10% of functionalized side chains and a thermally stable morphology.

2. The blend of claim 1, wherein a presence of functionalized side chains slows down a crystallization rate, not visible with DSC at 10 K min$^{-1}$, which stabilizes blend morphology.

3. The blend of claim 1, containing no photo-initiator.

4. The blend of claim 1, which is not crosslinked.

5. The blend of claim 1, wherein the polymer has monomer units according to formula (IV) and the at least one comonomer of formula (VII) in a ratio of from 3:2 to 1:49.

6. The blend of claim 1, wherein the polymer has monomer units according to formula (IV) and the at least one comonomer of formula (VII) in a ratio of from 3:2 to 1:19.

7. The blend of claim 1, wherein the polymer has monomer units according to formula (IV) and the at least one comonomer of formula (VII) in a ratio of from 1:4 to 1:19.

8. The blend of claim 1, wherein R is a linear alkyl group having from 6 to 10 carbon atoms.

9. The blend of claim 1, wherein R is a branched alkyl group having from 6 to 10 carbon atoms.

10. The blend of claim 1, wherein L is a linear alkylene group having 5 carbon atoms.

11. The blend of claim 1, wherein L is a branched alkylene group having 5 carbon atoms.

12. The blend of claim 1, wherein J is a hydrogen atom.

13. The blend of claim 1, wherein J is a linear alkyl group having from 1 to 4 carbon atoms.

14. The blend of claim 1, wherein J is branched alkyl group having from 1 to 4 carbon atoms.

15. The blend of claim 1, wherein a presence of functionalized side chains affects crystallization kinetics of the materials in the blend in such a way that no melting or crystallization can be detected with differential scanning calorimetry.

* * * * *